(12) United States Patent
Bongberg et al.

(10) Patent No.: US 9,035,787 B2
(45) Date of Patent: May 19, 2015

(54) CENTRALIZED MANAGEMENT AND EMERGENCY ALLOCATION OF DEPLOYED DEFIBRILLATORS EACH HAVING ASSOCIATED COMMUNICATION MODULES

(71) Applicants: Micah Bongberg, San Francisco, CA (US); Jan Gerritsen, San Francisco, CA (US); Walt Maclay, San Francisco, CA (US); John Hoving, San Francisco, CA (US); Mark Brinkerhoff, San Francisco, CA (US)

(72) Inventors: Micah Bongberg, San Francisco, CA (US); Jan Gerritsen, San Francisco, CA (US); Walt Maclay, San Francisco, CA (US); John Hoving, San Francisco, CA (US); Mark Brinkerhoff, San Francisco, CA (US)

(73) Assignee: NEW ANNUVIA COMPANY, LLC, San Francisco, CA (US)

( * ) Notice: Subject to any disclaimer, the term of this patent is extended or adjusted under 35 U.S.C. 154(b) by 0 days.

(21) Appl. No.: 14/210,427

(22) Filed: Mar. 13, 2014

(65) Prior Publication Data
US 2014/0266718 A1 Sep. 18, 2014

Related U.S. Application Data

(60) Provisional application No. 61/851,802, filed on Mar. 13, 2013.

(51) Int. Cl.
| | | |
|---|---|---|
| G08B 5/22 | (2006.01) | |
| G06Q 50/22 | (2012.01) | |
| A61N 1/39 | (2006.01) | |
| H04M 11/04 | (2006.01) | |
| G06Q 10/08 | (2012.01) | |
| G06F 19/00 | (2011.01) | |
| G09B 29/00 | (2006.01) | |

(52) U.S. Cl.
CPC ........ *G06Q 50/22* (2013.01); *A61N 1/39* (2013.01); *H04M 11/04* (2013.01); *G06Q 10/08* (2013.01); *G09B 29/007* (2013.01); *A61N 1/3968* (2013.01); *A61N 1/3993* (2013.01); *G06F 19/3418* (2013.01)

(58) Field of Classification Search
CPC ............... A61B 2560/0271; A61B 2560/02; G06F 19/3418
USPC ............... 607/142, 60, 5, 9; 600/301, 518; 340/815.45, 539.12, 539.1, 531, 540
See application file for complete search history.

(56) References Cited

U.S. PATENT DOCUMENTS

| | | | |
|---|---|---|---|
| 2003/0058097 A1* | 3/2003 | Saltzstein et al. | 340/531 |
| 2006/0092029 A1* | 5/2006 | Browne et al. | 340/573.1 |
| 2011/0205031 A1* | 8/2011 | Wakabayashi et al. | 340/10.41 |
| 2013/0087609 A1* | 4/2013 | Nichol et al. | 235/375 |

* cited by examiner

*Primary Examiner* — Vernal Brown
*Assistant Examiner* — Hongmin Fan
(74) *Attorney, Agent, or Firm* — Raj Abhyanker, P.C.

(57) ABSTRACT

A method, device and/or a system of centralized management and emergency allocation of deployed defibrillators each having associated communication modules. A central server may process a message from a communication module associated with a defibrillator, and then analyze a photograph and/or a video of a defibrillator display to compare it to a set of expected visual markers using a pixel algorithm of a pixel analysis module. The central server may then determine the operational status of the defibrillator such as whether it is in a nonfunctional status. The central server may then send alerts to the communication module and notifications to the an organization owning or leasing the defibrillator. The central server may also send alerts to the communication module based on a nearby emergency call, provide geospatial mapping of defibrillators to improve deployment efficiency and/or establish bi-directional communication between the operator of the defibrillator and a medical professional.

38 Claims, 9 Drawing Sheets

| MENU | LOCAL AED ID 600 | UNIQUE IDENTIFIER 112 | MAKER MODEL 602 | AED STATUS 606 | | LOCATION 612 | | SETTINGS 618 | COMMUNICATION MODULE BATTERY LIFE 620 | LAST SERVICED DATE 622 |
|---|---|---|---|---|---|---|---|---|---|---|
| MY AED NETWORK | | | | STATUS 608 | MESSAGE 610 | ASSOCIATION 614 | CURRENT GEOSPATIAL COORDINATES 616 | | | |
| SEND TECHNICIAN | 1 | SER.NO. 3478 | BRAND A MODEL 1 | OK | | OFFICE | X,Y | 1 CHECK/ DAY | 100% (PLUGGED-IN) | 9/12/2015 |
| REVIEW SUBSCRIPTION | 2 | SER. NO. T946 | BRAND B MODEL 1 | ERROR | CIRCUIT MALFUNCTION REVIEW | FACTORY 1 | X,Y | 1 CHECK/ DAY | 82% | 9/12/2015 |
| DESCRIPTION MAP | 3 | SER. NO. 4117 | BRAND A MODEL 1 | OK | | FACTORY 2 | X,Y | 1 CHECK/ DAY | 100% | 10/7/2016 |
| LEGAL COMPLIANCE | 4 | SER. NO. 66412 | BRAND B MODEL 2 | CHECK | BATTERY LOW SEND TECHNICIAN | DELIVERY TRUCK | X,Y | 1 CHECK/ DAY TEMP ALERT ON | 90% | 4/30/2016 |
| LOG AND AUDIT TRAIL | 5 | SER. NO. X275 | BRAND C MODEL 1 | IN FOR REPAIR | | RETAIL STORE | X,Y | 2 CHECKS/ DAY | N/A | 3/5/2014 |

DASHBOARD 115

ORGANIZATION DASHBOARD USER INTERFACE VIEW 650

FIGURE 6

CENTRALIZED MANAGEMENT AND EMERGENCY ALLOCATION OF DEPLOYED DEFIBRILLATORS EACH HAVING ASSOCIATED COMMUNICATION MODULES

CLAIMS OF PRIORITY

This patent application claims priority from U.S. Provisional patent application No. 61/851,802, filed Mar. 13, 2013, titled SYSTEM, METHOD AND APPARATUS FOR DETECTING STATUS INFORMATION FROM AN AUTOMATED EXTERNAL DEFIBRILLATOR.

FIELD OF TECHNOLOGY

This disclosure relates generally to data processing devices and, more particularly, to a method, device and/or a system of centralized management and emergency allocation of deployed defibrillators each having associated communication modules.

BACKGROUND

An organization (e.g. a business, a school, a hotel, a government agency) may have many defibrillators distributed across different physical buildings of the organization. Batteries in deployed defibrillators may expire at different times. In addition, sometimes defibrillators may be misplaced, tampered with, and/or require resetting. For this reason, the defibrillators may require regular maintenance to ensure operability during an emergency. Given the risks of non-functional defibrillators, the organization may need to comply with rules of regulatory bodies that govern safe and functional availability of defibrillators or restrictions of insurers of the organization.

The organization may hire a defibrillator serving organization to comply with rules of defibrillator maintenance. Individuals hired by the organization may not be able to find defibrillators that have been misplaced. Manual inspection of each defibrillator across the organization may be time consuming and inefficient. Further, sometimes defibrillators may become inoperable in between service intervals. During the emergency, a particular defibrillator of the organization closest to an individual in cardiac arrest may be unavailable and/or difficult to locate. As a result, the individual may die. This may expose the organization to civil liability and increased insurance costs. Most tragically, a life that could have been saved may be lost.

SUMMARY

Disclosed are a method, a device and/or a system of centralized management and emergency allocation of deployed defibrillators each having associated communication modules.

In one aspect, a monitoring system includes a defibrillator having a communication module to periodically generate a message based on an operational status of the defibrillator. The monitoring system also includes a network and a central server communicatively coupled with the communication module of the defibrillator through the network to analyze the message and/or to perform an action based on the operational status of the defibrillator.

The monitoring system may have the communication module to automatically enter an active mode from a sleep mode based on a predetermined time interval and/or to compress the message prior to communicating the message using a cellular network topology of the network in a manner such that a battery life of the communication module and/or the defibrillator is maintained for at least five years.

The battery may be powered through an alkaline zinc-manganese dioxide compound (Zn/MnO2), a rechargeable battery, a solar powered battery, and/or an alternating current source (A/C). The defibrillator may be enclosed in a housing in which the communication module is attached, and the housing may monitor the operational state of the defibrillator through a visual inspection of a display of the defibrillator that is enclosed in the housing.

The housing may be designed to operate across a wide range of defibrillator manufacturers such that defibrillators of different defibrillator manufacturers are each enclosed in housings having a common version of the communication module. The central server may monitor the operational status of a heterogeneous network of defibrillators made by different manufacturers without requiring normalization of disparate communication modalities. As a result, the disparate communication modalities of different manufacturers may be obviated due to the common version of the communication module.

Further, the housing may include a camera, a temperature sensor, a humidity sensor, a luminescence sensor, a clock, a timer, a global positioning circuit, a microphone, a speaker, an status light, and/or a display light. The camera, the temperature sensor, the humidity sensor, the luminescence sensor, the clock, the timer, the global positioning circuit, the microphone, the speaker, the status light, and/or the display light may activate when the communication module periodically enters the active mode from the sleep mode. The sleep mode may be a complete power down of the communication module.

The display light may illuminate the display based on a time of day as detected through the clock, a lumens value being below a threshold value as calculated by the luminescence sensor during the active mode of the communication module, and/or a visual readability of the display. The camera may take a photograph of the display and/or a video of the display to communicate the photograph of the display and/or the video of the display to the central server. The central server may then analyze the photograph of the display and/or the video to determine an operational status of the defibrillator using a pixel algorithm of a pixel analysis module based on a set of expected visual markers based on a model and/or a manufacturer of the defibrillator associated with the housing.

Additionally, the central server may determine that the communication module is in a functional state, a service state, a tampered state, an open state and/or a nonfunctional state. Similarly, the central server to determine that the defibrillator is in a functional status, a service status, a tampered status, an open status and/or a nonfunctional status.

The central server may also forward the photograph of the display and/or the video of the display to a state analyst to verify the operational status of the defibrillator when the central server determines that the defibrillator is in the service state, the tampered state, the open state, and/or the nonfunctional state. The central server may then supplement the set of expected visual markers with the photograph verified by the state analyst and/or the video verified by the state analyst to enhance a veracity of an operational status determination analysis by the central server.

The communication module may override the periodic awakening in order to automatically enter the active mode from the sleep mode when the defibrillator is in the open state. The central server may also establish a bi-directional communication through the cellular network between a medical professional and/or an operator of the defibrillator when the defibrillator is in the open state. The predetermined time interval may be one day.

The central server may also determine a present geo-spatial location of the defibrillator using the global positioning circuit and/or a cellular device triangulation of the communication module. The central server may also automatically generate an audio command/or to sound an audio alarm through the speaker of the housing when a 911 emergency call is detected in a geospatial vicinity closest to a defibrillator having an internal version of the communication module and/or an external version of the communication module in the housing. The audio alarm may also sound in alternatively a different audio frequency and/or tone when the defibrillator is in need of service.

The central server may automatically generate a status command in order to illuminate the status light of the housing when the 911 emergency call is detected in the geospatial vicinity closest to the defibrillator having the internal version of the communication module and/or the communication module in the housing. The status light may also illuminate in alternatively a different color and/or alternatively in a blinking pattern when the defibrillator is in need of service.

The central server may also assess a subscription fee to an organization that at least one owns and/or leases the defibrillator. The subscription fee may be based on a set of features desired by the organization, a service frequency, and/or a total number of installed defibrillators monitored by the central server on behalf of the organization.

The central server may automatically dispatch a technician to either reset defibrillators and/or repair defibrillators that are in the service status, the tampered status, the open status and/or the nonfunctional status.

The central server may provide a dashboard view to the organization such that the organization is permitted to view operational statuses of defibrillators deployed at different geospatial locations of the organization simultaneously. In addition, the central server may automatically maintain an audit trail of defibrillators to maintain regulatory compliance based on the dashboard view, and may periodically process a series of messages from communication modules of deployed defibrillators associated with the organization. Each one of the communication modules each include a unique identifier. The central server may also determine the operational status of each of the deployed defibrillators based on an analysis of the series of messages with a lookup table based on the model and/or the manufacturer of each one of the deployed defibrillators as determined through the unique identifier of each one of the communication modules.

In another aspect, the method of a central server includes processing a message generated by a communication module of a defibrillator associated with an organization. The communication module includes a unique identifier. The central server may also determine a manufacturer and/or a model of the defibrillator through a lookup table associating the manufacturer and/or the model with the unique identifier of the communication module. The central server then analyzes a photograph and/or a video taken by the communication module of the defibrillator based on a set of expected visual markers. The set of expected visual markers are based on the manufacturer and/or the model of the defibrillator.

Next, the central server determines an operational status of the defibrillator based on a comparison of the photograph and/or the video to the set of expected visual markers using a pixel algorithm of a pixel analysis module. The central server then determines that operational status of the defibrillator is at least one of a functional status, a service status, a tampered status, an open status and/or a nonfunctional status.

In yet another aspect, a monitoring system includes a defibrillator having a communication module to periodically generate a message based on an operational status of the defibrillator and a network. The system also includes a central server communicatively coupled with the communication module of the defibrillator through the network. The central server analyzes the message and/or performs an action based on the operational status of the defibrillator. Specifically, the central server periodically process a series of messages from communication modules of deployed defibrillators associated with an organization, each one of the communication modules each including a unique identifier. The central server also determines the operational status of each of the deployed defibrillators based on an analysis of the series of messages with a lookup table based on the model and/or the manufacturer of each one of the deployed defibrillators as determined through the unique identifier of each one of the communication modules.

BRIEF DESCRIPTION OF THE DRAWINGS

The embodiments of this invention are illustrated by way of example and not limitation in the figures of the accompanying drawings, in which like references indicate similar elements and in which:

FIG. 6 is an organization dashboard user interface view 650 which shows a browser-based user interface of a dashboard presented to the organization of FIG. 1 such that an agent of the organization may review the heterogeneous network of defibrillators, including a unique identified of the defibrillator, a status of the defibrillator, a current geospatial location, a settings, a communication module battery life, and a last serviced date, according to one or more embodiments.

Figure 1:
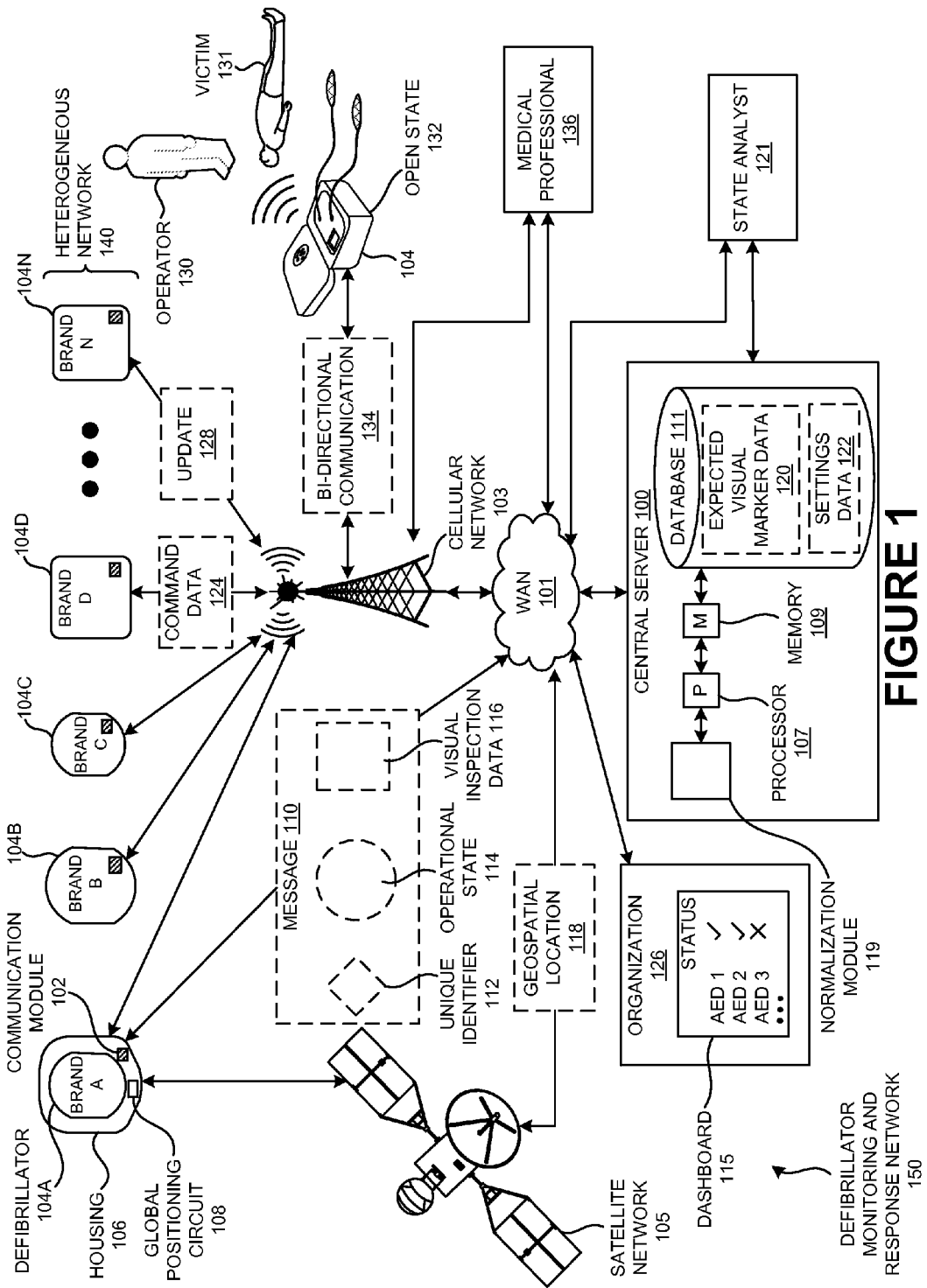
FIG. 1 is a defibrillator monitoring and response network in which a defibrillator with an associated communication module within a heterogeneous network of defibrillators communicates a message related to an operational status of the defibrillator through a network to a central server which analyzes the message with a pixel algorithm to determine the operational status, the central server operable to: forward a visual inspection data of the message to an analyst for verification of the operational status; update an organization owning or leasing the defibrillator as to the operational status; and send a command data back to the defibrillator; and/or initiate a bi-directional communication between an operator of the defibrillator and a medical professional, according to one or more embodiments.

Other features of the present embodiments will be apparent from the accompanying drawings and from the detailed description that follows.

DETAILED DESCRIPTION

Disclosed are a method, a device and a system of centralized management and emergency allocation of deployed defibrillators each having associated communication modules. Although the present embodiments have been described with reference to specific example embodiments, it will be evident that various modifications and changes may be made to these embodiments without departing from the broader spirit and scope of the various embodiments.

A defibrillation may be a common treatment for a subset of life-threatening cardiac dysrhythmias, ventricular fibrillation and/or pulseless ventricular tachycardia. A defibrillator may be a device that accomplishes defibrillation by delivering a therapeutic dose of electrical energy to the heart of a victim. The therapeutic shock may depolarize a critical mass of the heart muscle, terminate the dysrhythmia and may allow normal sinus rhythm to be reestablished by the body's natural pacemaker, in the sinoatrial node of the heart. Some external defibrillators, which may be known as automated external defibrillators (AEDs), may automate the diagnosis of treatable rhythms, meaning that lay responders or bystanders may be able to use the AED successfully with little or no training.

AEDs may be held by trained personnel who may respond to a medical incident (e.g., police officers, security guards, park rangers), or may be publicly accessible units which may be found in places such as corporate and government offices, shopping centers, airports, restaurants, casinos, hotels, sports stadiums, schools, universities, community centers, fitness centers and health clubs.

AEDs may also be located on transportation vehicles such as delivery trucks, trains, commercial airlines and cruise ships. In addition, some communities may have dedicated community first responders, who may volunteer to keep an AED and respond to a victim in their area. In general, the locating of one or more publically accessible AEDs may take into account where large groups of people gather, and the risk category associated with these people.

An organization (for example a corporation, a university, a small business, a shipping company with a fleets of vehicles, a government agency such as the Environmental Protection Agency or the Federal Bureau of Investigation, an international organization such as the United Nations) may have a large number of defibrillators deployed throughout one or more territorial jurisdictions (e.g., counties, states, nations). These deployed defibrillators may be a heterogeneous network of defibrillators because new, more reliable models may be purchased as the organization grows without the complete displacement of the existing defibrillator units. Similarly, the organization may purchase different defibrillators having different features advantageous to certain deployment environments.

Managing these defibrillators may be a challenge due safety recalls by the Food and Drug Administration (FDA) or the manufacturer, the need to replace parts (such as batteries and pads that may periodically expire), and other degradations requiring attention by a trained technician such as internal circuitry malfunctions. Effectively managing the defibrillators, however, may be important not only to maximize the chance the defibrillator may save a life when called upon, but to invoke the "good Samaritan laws" of the relevant jurisdiction such that an operator of the defibrillator and/or the organization is shielded from legal liabilities. One strategy to manage the defibrillators may be a periotic on-site inspection by technicians. This inspection of the organization's network of AED's may be expensive, time consuming, and unreliable.

FIG. 1 is a defibrillator monitoring and response network in which a defibrillator with an associated communication module within a heterogeneous network of defibrillators communicates a message related to an operational status of the defibrillator through a network to a central server which analyzes the message with a pixel algorithm to determine the operational status, the central server operable to: forward a visual inspection data of the message to an analyst for verification of the operational status; update an organization owning or leasing the defibrillator as to the operational status; and send a command data back to the defibrillator; and/or initiate a bi-directional communication between an operator of the defibrillator and a medical professional, according to one or more embodiments. Particularly, FIG. 1 illustrates a central server 100, a wide area network (WAN) 101, a communication module 102, a cellular network 103, a defibrillator 104 and a heterogeneous network 140 of a set of defibrillators 104A through 104N, a satellite network 105, a housing 106, a processor 107, a global positioning circuit 108, a memory 109, a message 110 (which be comprised of a unique identifier 112, an operational state 114, and a visual inspection data 116), a database 111, a dashboard 115, a geospatial location 118, a normalization module 119, an expected visual marker data 120, a state analyst 121, a settings data 122, a command data 124, an organization 126, an update 128, an operator 130, a victim 131 of a cardiac arrest, an open state 132 of the defibrillator 104, a bi-directional communication 134, and a medical professional 136.

The central server 100 may be communicatively coupled to the communication module 102 of the defibrillator 104 and/or each of defibrillators 104A through 104N in the heterogeneous network 140 of defibrillators through one or more communication networks, for example the wide area network 101, the cellular network 103, and/or the satellite network 105 (collectively referred to herein as "the communication network"). The defibrillator 104 may be an automatic external defibrillator (AED), a manual external defibrillator, or a semi-automatic external defibrillator. In a preferred embodiment, the defibrillators 104A through 104N may be comprised primarily of automatic external defibrillators.

In one embodiment, the communication module 102 may be attached to or contained within the defibrillator 104 (as shown in defibrillators 104B through 104N). In another embodiment, the communication module 102 may be contained in a housing 106 of the defibrillator 104 (as shown in defibrillator 104A). The housing 106 may be attached to the defibrillator 104 and/or enclose the defibrillator 104. For example, the housing 106 may be a specialized cabinet for storing the defibrillator 104 in a public location or may be a carrying case to protect the defibrillator 104 from adverse weather conditions or damage. Incorporating the communication module 102 into the housing 106 may allow the organization distributing the defibrillators 104A through 104N to associate communication modules 102 with defibrillators 104 that would not otherwise have the ability to communicate information associated with the operational status of the defibrillator 104 to the central server 100.

A bus communicatively coupling the communication module 102 and the central server 100 may be the communications network. The cellular network 103 may be a mobile network and/or a wireless network distributed over land areas that may be referred to as cells, each cell served by at least one fixed-location transceiver, known as a cell site or base station, the cells providing wide geographic coverage area when linked together to form a topology. The wide area network 101 may be a network that covers a broad area using private or public network transports (for example, the Internet). The satellite network 105 may be a plurality of satellites within the Global Positioning System (GPS), which may be a space-based satellite navigation system that provides location and time information in all weather conditions, anywhere on or near Earth.

Figure 3:
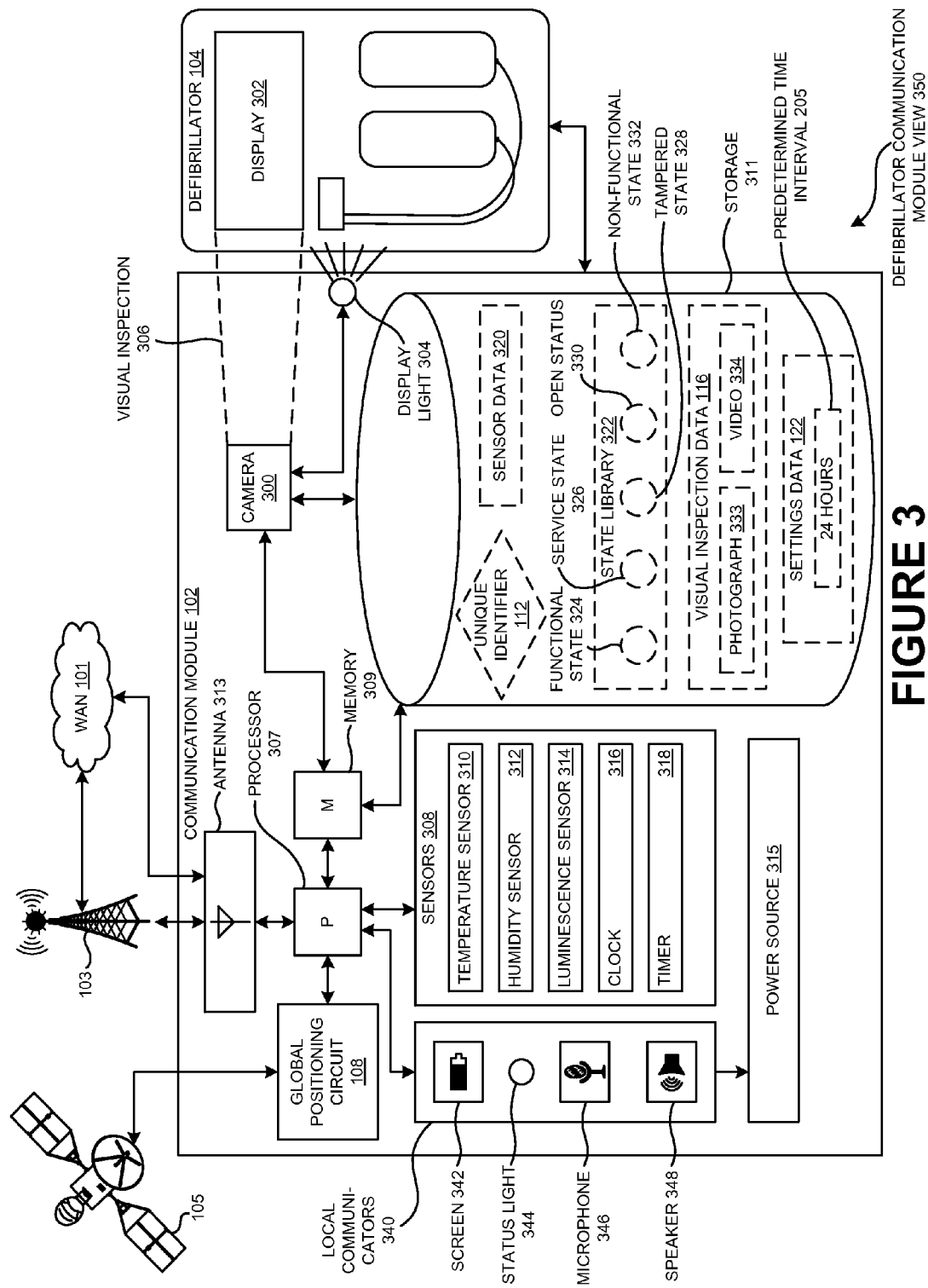
FIG. 3 is a defibrillator communication module view that shows the communication module of FIG. 1 comprised of a power source, a display light to illuminate a display of the defibrillator that is associated with the communication module, a camera to capture the display, a set of local communicators to communicate the status of the communication module to people in the presence of the communication module, and an antenna and/or a global positioning circuit to communicate with the central server of FIG. 2 through the network of FIG. 1, according to one or more embodiments.

As shown in FIG. 3 and described in the accompanying text, the communication module 102 may generally exist in a sleep mode (e.g., in a standby mode or a completely powered down mode) in order to conserve a power source of the communication module, for example a battery. The communication module 102 may periodically awaken to generate the message 110 and communicate with the central server 100. For example, the communication module 102 may be programmed to connect to the central server 100 through the WAN 101, the cellular network 103, and/or the satellite network 105, twice per day, once per day, once per week, or once per month. In addition, a person in the presence of the communication module 102 may initiate a connection between the communication module 102 and the central server 100 by, for example, opening the housing 106 (such that it is in the open state 132), opening the defibrillator 104, or pressing a button associated with the communication module 102 (e.g., to force a manual "wake up" or a manual initiation of a "self diagnostic" function).

The defibrillator 104 may send the message 110 (which may contain the unique identifier 112 of the communication module 102 and/or the defibrillator 104, the operational state 114 of the communication module 102 and/or the defibrillator 104, and/or the visual inspection data 116 of the defibrillator 104) through the cellular network 103 and/or the WAN 101 to the central server 100 for analysis. As used herein, "operational status" may refer to the condition of the defibrillator, whereas "operational state" may refer to the communication module 102. The message 110 may also include a sensor data (not shown in FIG. 1) from one or more sensors of the communication module 102 (e.g., the humidity sensor 312 of FIG. 3). In addition, the geospatial location 118 of the defibrillator 104 may be sent from the global positioning circuit 108 through the satellite network 105 to the central server 100. In addition, the geospatial location 118 may be obtained by a triangulation of the base stations of the cellular network 103, as show and describing in conjunction with FIG. 9.

The contents of the message 110 may be processed by the central server 100 to determine the operational state of the communication module 102 and/or the operational status of the defibrillator 104. Specifically, the central server 100 may analyze the operational state 114 of the message 110 and/or may analyze the visual inspection data 116 of the defibrillator 104 and compare the visual inspection data 116 to the expected visual marker data 120, as shown and discussed in conjunction with FIG. 4. The central server 100 may be able to analyze the heterogeneous network 140 of defibrillators 104A through 104N through use of the normalization module 119. The normalization module 119 may process the contents of the message 110 such that any make or model of the defibrillator 104 may be analyzed, as also shown and described in conjunction with FIG. 4. Although the embodiment of FIG. 1 demonstrates the heterogeneous network 140 communicating with the central server 100, the network within the organization 126 of defibrillators 104 having associated communication modules 102 may be a homogeneous network (that is, a defibrillator deployment network containing a uniform type of make and/or model of the defibrillator 104). For verification of an adverse state of the defibrillator 104, or to resolve a visual distortion of the visual inspection data 116, part or all of the message 110 may be automatically relayed to the state analyst 121, as shown and discussed in conjunction with FIG. 5.

After analyzing the operational state 114 and/or the operational status of the defibrillator 104 and finding a positive condition (e.g., no major condition of adversity), the central server may take no major action and may cease to communicate with the communication module 102, allowing it to return to the inactive status. In such case, some or all of the contents of the message 110 and a meta data associated with the message 110 may be logged and an update may be sent to the dashboard 115 of the organization 126. However, should the central server 100 determine that the operational state 114 of the communication module 102 and/or the defibrillator 104 is in an adverse state (e.g., a low battery condition, a circuitry malfunction, an out of network range condition), the central server 100 may take a number of actions to alert one or more people who may be in the vicinity of the communication module 102 by triggering a set of indicators of the communication module 102 and/or notifying the organization on the dashboard 115. The central server 100 may communicate some or all of the message 110, along with relevant expected visual marker data 120, to the state analyst 121 for verification. The central server 100 may also send the command data 124 through the WAN 101 and/or cellular network 103 to activate alarms (e.g., a chirping noise may occur in smoke detectors) and/or status lights (e.g., a red light easily visible on the exterior of the housing 106 to indicate that the communication module 102 and/or the defibrillator 104 is experiencing a malfunction) associated with the communication module 102. As discussed below, the command data 124 may solicit a set of additional responses of the communication module 102 and/or the defibrillator 104 useful to the operator 130 of the defibrillator 104 when the defibrillator 104 containing the communication module 102 is in the open state 132 (or, alternatively, when the housing 106 containing the communication module 102 is in the open state).

Should the operational state 114 of the communication module 102 and/or the defibrillator 104 be in the adverse state, the central server 100 may also relay an adverse update to the dashboard 115 of the organization 126. The central server may also log all data associated with the message 110 generating the adverse state, and automatically notify and/or dispatch a technician to the location of the defibrillator 104 (e.g., by conveying to the technician the geospatial location 118). The technician may be an internal technician of the organization, a technician employed by the operator of the central server, a medical professional, or an individual knowledgeable of defibrillators (e.g., a volunteer technician as may be required to inspect the defibrillator 104 in a small rural community) and/or a third-party service contractor. The organization 126 may request the dispatch of the technician through use of the dashboard 115, as show and described in conjunction with FIG. 6.

In addition to sending the command data 124, the central server 100 may send the update 128 which may be an update such as a firmware patch, a software upgrade, and/or new instances of the settings data 122. The settings data 122 may set a predetermined time interval in which the communication module 102 attempts to connect to the central server 100, or may adjust optical parameters of a flash and/or a camera associated with generation of the visual inspection data 116. Additionally, when the communication module 102 is integrated into the defibrillator 104, the update 128 may cause changes within the defibrillator 104, such as disabling the defibrillator 104 (e.g., when there has been a safety recall of the specific make and model), changing a voltage to be administered in accordance with a new set of safety regulations and/or altering the parameters of heart-malfunction detection in accordance with a novel scientific report or a new set of promulgated guidelines. Disabling the defibrillator 104 may be especially important because they may have been over 700 deaths in the 5 year period between 2004 and 2009 associated with automatic external defibrillators, which may have primarily been cause by component failures or design errors. During this time period, up to 70 types of AEDs may have been recalled, including recalls from every AED manufacturer in the world.

In addition to facilitating the maintenance and regulatory compliance of the heterogeneous network 140 of the organization 126 such that the defibrillators 104 are in top working condition, the central server 100 may additionally receive the message 110 and the geospatial location 118 of the defibrillator 104 and/or housing 106 that is in the open state 132 (e.g., has been opened to respond to a medical emergency). The communication module 102 may relay the message 110 at the time the defibrillator 104 enters the open state 132 or at any time after the open state 132 begins. In addition, multiple and/or continuous messages 110 may be relayed as battery conservation may be of little concern during the emergency. The message 110 may include additional data such as diagnostic information collected from the defibrillator 104 in the open state 132 once a set of pads associated with the defibrillator 104 are placed on the victim 131.

The message 110 of the defibrillator 104 in the open state 132 may also include with the open state 132 as a status indicator. The central server 100, upon receipt of the open state 132 indicator, may send the command data 124 to activate the alarm and/or a speaker associated with the communication module 102 to direct people in the vicinity of additional deployed defibrillators 104 receiving the command data 124 to convey addition of the defibrillators 104 receiving the command data 124 to the nearby operator 130 of the defibrillator 104 in the open state 132 to maximize the chance a functional unit of the defibrillator 104 may respond to the medical emergency.

Figure 9:
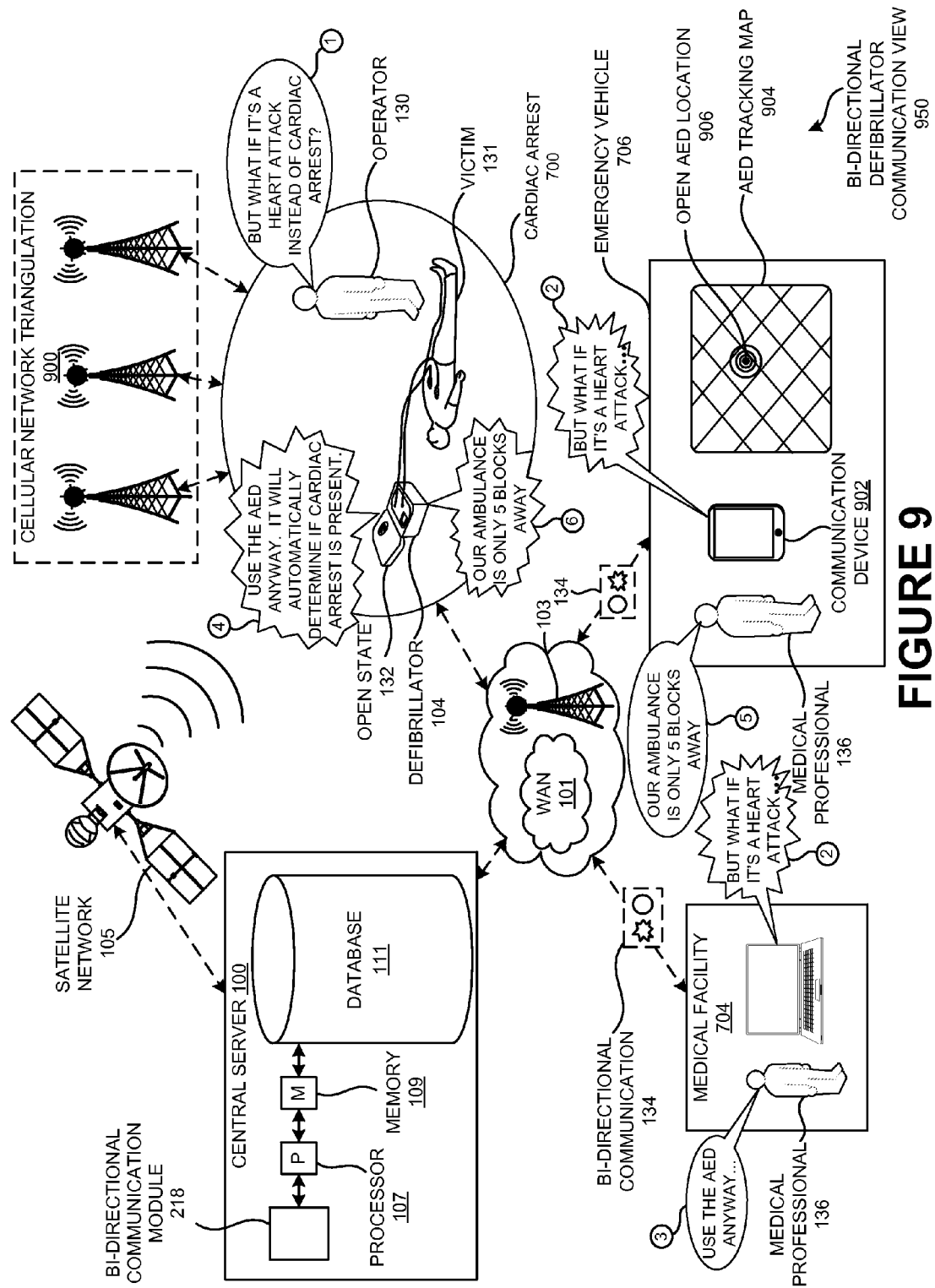
FIG. 9 is a bi-directional defibrillator communication view which shows a defibrillator in use by an operator attempting to save a victim, a bi-directional communication of the defibrillator forming between the operator and one or more medical professionals associated with a medical facility and/or an emergency vehicle, a cellular network triangulation conveying an open AED location to the medical professional, the bi-directional communication additionally giving confidence to the operator such that operator uses the defibrillator in the absence of the medical professionals, according to one or more embodiments.

In one preferred embodiment, as shown and described in conjunction with FIG. 9, the communication module 102 may have the capability to initiate a bi-directional communication 134 between the operator 130 of the defibrillator 104 in the open state 132 and the medical professional 136. The bi-directional communication 134 may be mediated by the central server 100 or may occur directly between the operator 130 and the medical professional 136 through the network (e.g., the cellular network 103).

Figure 2:
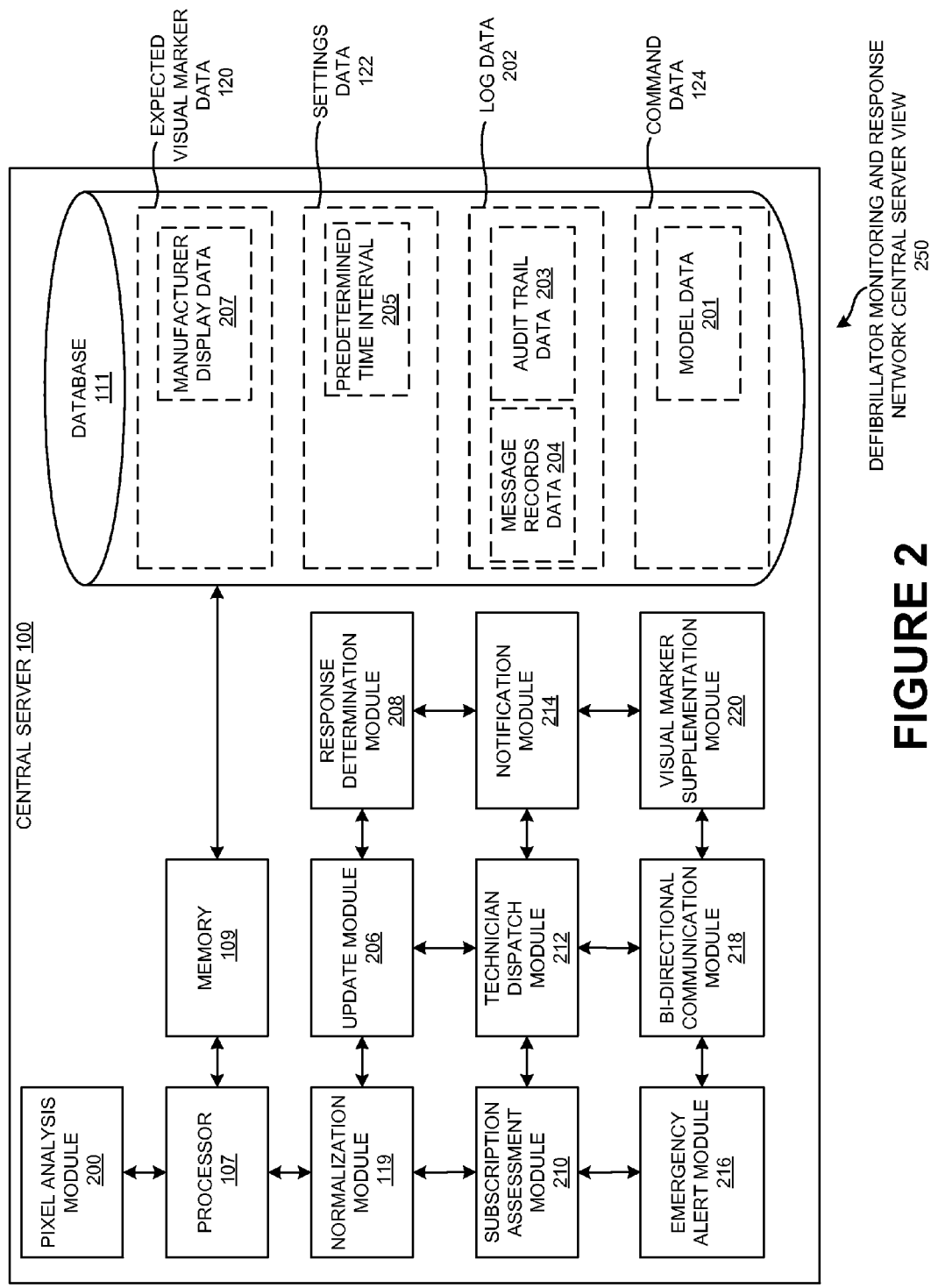
FIG. 2 is a defibrillator monitoring and response network central server view which shows the central server of FIG. 1 having a processor, a memory, a collection of modules to carry out the operations of the defibrillator monitoring and response network including the pixel analysis module applying the pixel algorithm, and a database, the database comprising an expected visual markers data, a settings data, a log data, and a command data, according to one or more embodiments.

FIG. 2 is a defibrillator monitoring and response network central server view which shows the central server of FIG. 1 having a processor, a memory, a collection of modules to carry out the operations of the defibrillator monitoring and response network including the pixel analysis module applying the pixel algorithm, and a database, the database comprising an expected visual markers data, a settings data, a log data, and a command data, according to one or more embodiments. Particularly, FIG. 2 further illustrates a pixel analysis module 200, a model data 201, a log data 202 which may include an audit trail data 203 and a message records data 204, a predetermined time interval 205, an update module 206, a manufacturer display data 207, a response determination module 208, a subscription assessment module 210, a technician dispatch module 212, a notification module 214, an emergency alert module 216, a bi-directional communication module 218, and a visual marker supplementation module 220.

The database 111 may contain a number of data items which may aid in analysis of the message 110, the issuance of the command data 124, the sending of the update 128, and/or the establishment of the bi-directional communication 134. Associated with the expected visual marker data 120 may be the manufacturer display data 207 which may contain screen shots of each possible display icon on a display screen of a particular defibrillator 104's make and model. For example, the "low battery" indicator for Brand A may be a battery symbol displayed on an LCD display screen. On the other hand, Brand B may activate a red LED light. Each make and model of defibrillator within the heterogeneous network 140 may therefore have its own set expected visual markers, each corresponding to one or more instances of the defined operational status that may trigger the command data 124, verification by the state analyst 121, sending of the update to the dashboard 115, and/or additional reactions carried out by the central server 100.

The log data 202 may include data log files about the messages 110 and/or geospatial location 118 received from the defibrillators 104A through 104N of the heterogeneous network 140. For example the log data 202 may include the message records data 204 such as a sensor data of the communication module 102, the operational state 114, the visual inspection data 116, the unique identifier 112, a current version of the software and hardware used by the defibrillator 104 and/or communication module 102, and additional useful information. In addition, the log data may record metadata such as a time and a date of receipt of the message and/or the connection strength of the communication module 102 to one or more of the networks. The log data 202, including the message records data 204, may be organized into the audit trail data 203. The audit trail data 203 may be a security-relevant chronological record and/or destination and source of records that provide documentary evidence of the sequence of activities (e.g. receipt of the message 110 and the geospatial location 118) that have affected at any time a specific operation, procedure, or event of the defibrillator monitoring and response network.

The settings data 122 may contain a set of preferences for the individual elements of the communication module 102 and/or the defibrillator 104. For example, the settings data 122 may include the predetermined time interval 205 which may be sent to each of the defibrillators 104 in order to set them to connect to the central server 100 at the predetermined time interval 205. The organization 126 may be able to set the predetermined time interval 205, or an other setting within the settings data 122 through the dashboard 115. Additional instances of the settings data 122 may include, for example: the brightness of a flash LED to light a display of the defibrillator 104 display during generation of the visual inspection data 116; whether the visual inspection data 116 should be comprised of one photograph, several photographs, or a video; the intensity of audible and/or visual alarms initiated by the command data 124; and/or which information the communication module 102 should include in the message 110.

The command data 124 includes a set of commands required to manipulate the communication module 102 and/or the defibrillator 104 having an integrated communication module 102. A common version of the communication module 102 may be associated with several versions of the housing 106, each designed to fit a different make and model of the defibrillators 104 within the heterogeneous network 140. When the communication module 102 is integrated into the housing 106, the communication module 102 may not directly communicate with the defibrillator 104 other than to collect the visual inspection data 116. In such case, a common version or a family of related versions of the communication module 102 may exist in two or more of the housings 106. The command data 124 may include commands that initiate actions in the communication module 102 associated with the external portion of the housings 106. In addition, the command data 124 may also contain model data 201 that may be unique to each make and model's communication module 102 when the communication module 102 is integrated into the defibrillator 104.

The normalization module 119 may examine the unique identifier 112 of the message 110 to determine the make, the model and/or the version of the communication module 102 and/or the defibrillator 104. Where the communication module 102 is not integrated into the defibrillator 104, the normalization module 119 may reference a lookup table tying the unique identifier 112 to the particular housing 106 which may be unique to a make and model of the defibrillator 104. Additionally, the normalization module 119 may work in conjunction with the pixel analysis module 200 to compare the visual inspection data 116 to all instances of the manufacturer display data 207. After determining which make and model of the defibrillator 104 to analyze the normalization module 119 may compare any contents of the message 110 with the appropriate make and model markers that may be generated by sensors of the communication module 102 (as shown and described in conjunction with FIG. 4) (e.g., a low battery of the communication module 102, a temperature below 30 degrees F., etc.).

The pixel analysis module 200, after the normalization module 119 may determine the appropriate version of the manufacturer display data 207 of the expected visual marker data 120 for the pixel analysis module 200 to analyze, may compare the visual inspection data 116 to the manufacturer display data 207 to determine a match between the visual inspection data 116 and a record marker of the manufacturer display data 207.

Specifically, the pixel analysis module 200 may apply a pixel algorithm to analyze the visual inspection date. In one embodiment, the pixel algorithm may operate as follows. First, the pixel algorithm may determine whether a first pixel in a target image matches a corresponding pixel in a control image using a tolerance checking method. Further, the pixel algorithm may utilize an image comparison algorithm based on a rasterization technique in which each pixel is compared against neighboring pixels from the first line of the rasterization to the last, in a horizontal zig-zag comparison. If a threshold number of pixels of the target image are correlated beyond a threshold of 0.95 confidence between the target image and the control image, the pixel algorithm may yield a 'pass' status, indicating that the defibrillator is currently in an operational status and thus safe to remain deployed. In one embodiment, the target image is compared against a set of control images comprising a number of operational states of the defibrillator device.

In contrast, if a threshold number of pixels of the target image are not correlated beyond a threshold of 0.95 confidence between the target image and the control image, the pixel algorithm may yield a "fail status," indicating that the defibrillator is not currently operational and active in that particular control state. Then, each control image in the set of control images may be considered against the target image until a match is determined. One control image may be a null image in which there is a complete single color pixilation. In such a state, the control image may be the default, when there is no power to the defibrillator, and thereby indicating an off status of the defibrillator.

In another aspect, the pixel algorithm may be applied at both the communication module 102 and the central server 100. This process works as follows. First, a plurality of template color values, with each template color value representing a different color, may be created and/or defined and planted on the storage. Second, the communication module 102 may take a digital picture (e.g., the photograph 333 and/or the video 134). The digital picture may be stored as a first plurality of pixel color values in a storage (e.g., the storage 311 of FIG. 3) of the communication module 102. The communication module 102 may processing the first plurality of pixel color values to create a second plurality of pixel color values and store the second plurality of pixel color values in the storage.

Next, a three-dimensional space representing the shortest distance between each template color value within the plurality of template color values and each pixel color value within the second plurality of pixel color values may be calculated. The process may then identifying each pixel color value within the second plurality of pixel color values an associated template color value out of the plurality of template color values having the shortest distance to the each pixel color value; setting said each pixel color value to equal its associated template color value; and storing the result as a third plurality of pixel color values. At least one pixel color value within the third plurality of pixel color values may be set equal to a null value.

Finally, the pixel algorithm may determining the readiness and/or operational status of the defibrillator by calculating the numerical ratio of the number of pixel color values within the third plurality of pixel color values having a predetermined first color value to the number of pixel color values within the third plurality of pixel color values having a predetermined second color value, with neither the first color value nor the second color value having a null value.

As a result of the application of the pixel algorithm, an alert signal based on the determination of the defibrillator status may be sent to the communication module 102, the organization 126, the state analyst 121, and/or the medical professional 136. Additionally, the digital picture for the readiness screen stored as a first plurality of pixel color values may be forwarded to the state analysis 121 and/or the organization 126.

The record marker may be one of many predefined instances within expected visual marker data 120, such as an exemplar photograph. The update module 206 may analyze the version of the communication module 102 at the time of the periodic connection between the communication module 102 and the central server 100, and may send updated firmware and/or software to the communication module 102. Where the communication module 102 is integrated into the defibrillator 104, the update module 206 may also send firmware and/or software updates to the defibrillator 104.

The response determination module 208 may determine, based upon the determination of the pixel analysis module 200 applying the pixel algorithm, which instance of the command data 124 should be sent to the communication module 102, which notification should be sent to the dashboard 115 and or additional responses by the central server 100 should be carried out. The notification module 214 may transmit the command data 124 to the communication module 102, the notifications to the dashboard 115, and may additionally send out any other notifications. The visual marker supplementation module 220 may allow the state analyst to add a new expected visual marker to the expected visual marker data 120 such that a visual inspection data 116 matching the new expected state marker will not trigger the adverse determination by the central server 100, as shown and described in conjunction with FIG. 5.

The subscription assessment module 210 may be used to asses subscription fees to the organization 126 for having communication modules 102 connected to the defibrillator monitoring and response network 150. Subscription fees may be assessed, for example, the number of communication modules 102 or defibrillators 104 deployed, the number of periodic connections made to one or more networks, the amount of data transferred over the network of an on-site service plan to response to adverse conditions, and/or which features the organization would like to have enabled (e.g., defibrillators that have bi-directional communication capability).

The technician dispatch module 212 may automatically notify a technician when the communication module 102 of the defibrillator 104 is determined by the central server 100 to be in an adverse state (or, for example, when a given defibrillator known by the central server 100 does not "check in" during the predetermined time interval 205). The technician dispatch module 212 may additionally wait for input from the dashboard 115 of the organization 126 as to whether to dispatch the technician.

Figure 7:
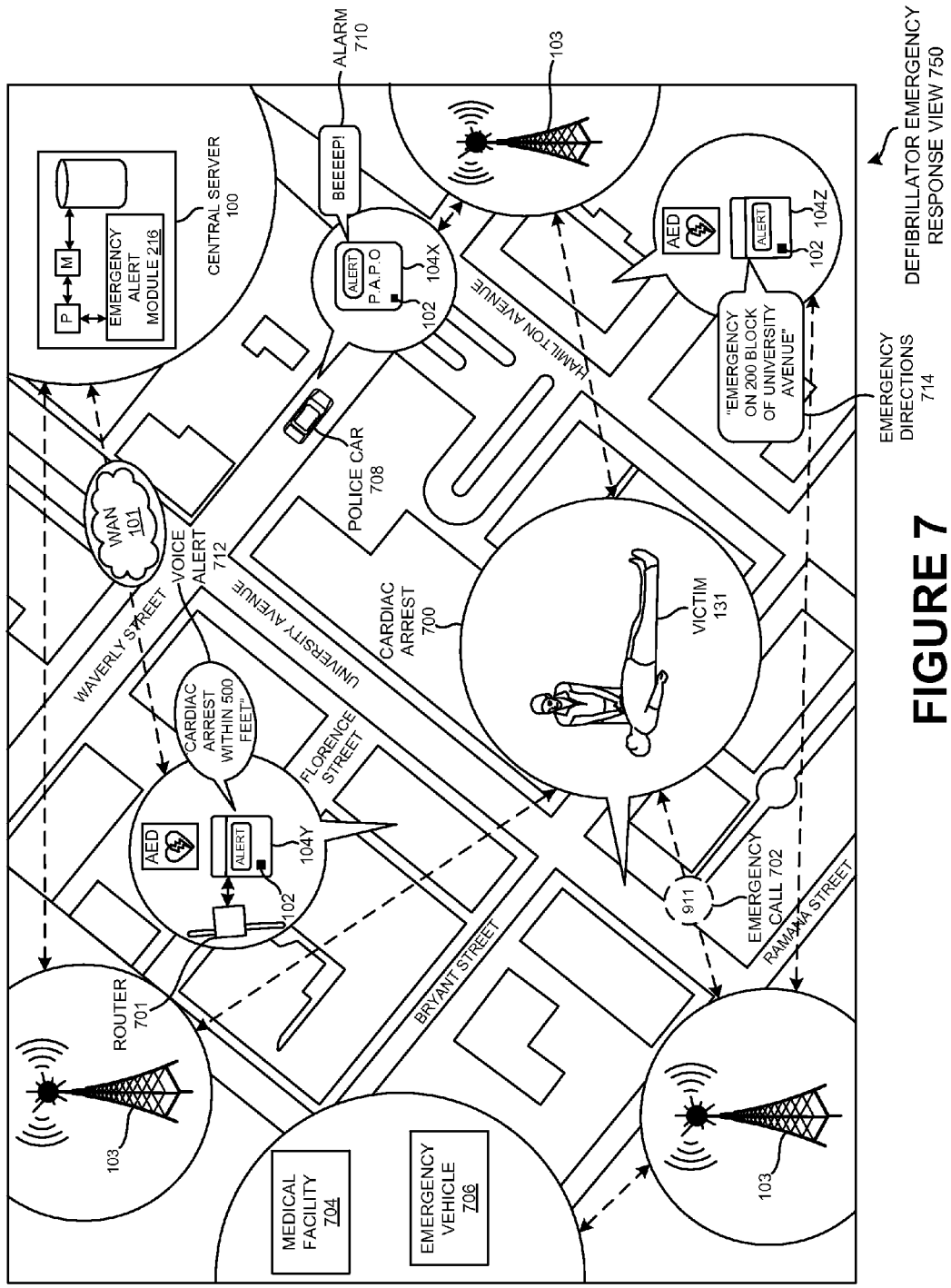
FIG. 7 is a defibrillator emergency response view which shows a medical incident in which a victim may be suffering from a cardiac arrest, the medical incident precipitating an emergency call to a medical facility and automatically triggering nearby defibrillators, through the central server communicatively coupled to the network receiving the emergency call, to sound a response such as an alarm, a voice alert, and a set of emergency directions, according to one or more embodiments.

The emergency alert module 216 may analyze the geospatial coordinates of a medical emergency and send command data 124 activating a set of communication modules 102 nearby the medical emergency, as shown and described in conjunction with FIG. 7. The bi-directional communication module 218 may connect the communication module 102 with the medical professional 136 when the housing 106 associated with the communication module 102 is in the open state 132 and/or when the defibrillator 104 is in the open state 132, as shown and described in conjunction with FIG. 9.

FIG. 3 is a defibrillator communication module view that shows the communication module of FIG. 1 comprised of a power source, a display light to illuminate a display of the defibrillator that is associated with the communication module, a camera to capture the display, a set of local communicators to communicate the status of the communication module to people in the presence of the communication module, and an antenna and/or a global positioning circuit to communicate with the central server of FIG. 2 through the network of FIG. 1, according to one or more embodiments. In particular, FIG. 3 further illustrates a camera 300, a display 302 of the defibrillator 104, a display light 304, a visual inspection 306 of the display 302, a processor 307, a set of sensors 308 (comprised of a temperature sensor 310, a humidity sensor 312, a luminescence sensor 314, a clock 316, and a timer 318), a memory 309, a storage 311, an antenna 313, a power source 315, a sensor data 320, state library 322 (comprised of a functional state 324, a service state 326, a tampered state 328, an open status 330, and a non-functional state 332), a photograph 333, a video 324, a set of local communicators 340 (comprised of a screen 342, a status light 344, a microphone 346, and a speaker 348). The communication module 102 of the embodiment of FIG. 3 not integrated into the defibrillator 104. While the communication module of FIG. 3 may be integrated into and/or attached to the housing 106, the housing 106 is excluded for illustrative purposes.

The camera 300 may make the visual inspection 306 of the display 302 of the defibrillator 104. The visual inspection 306 may generate the visual inspection data 116 which may be placed in the storage 311 and which may comprise the photograph 333 and/or the video 334. The video 334 may be a series of photographic captures, a frame rate of the captures sufficient to capture a periodically blinking indicator of the display 302 (e.g., a blinking light as appearing in both an "on" and an "off" position that a single photograph may fail to capture). The video 334 may also be a high frame rate (30+ frames per second). The display 302 may be a screen such as an LCD screen or any other indicator (e.g., an LED light) meant to convey information about the operational state of the communication module 102 and/or the operational status of the defibrillator 14 when integrated with the communication module 102. The camera 300 may be assisted in accomplishing the visual inspection 306 by use of the display light 304, which may be an LED light (or any other suitable light source) positioned and angled such that the camera 300 may accurately capture an information that may be presented or shown on the display 302 relating to the operational status.

Communicatively coupled to the storage 311 may be the processor 307, the memory 309, the set of sensors 308, the local communicators 340, the global positioning circuit 108, and the power source 315. The local communicators 340 may be indicators that convey an information about the operational state of the communication module 102 and/or the operational status of the defibrillator 104. The local communicators 340 may include a screen 342 (e.g., an LCD screen) that may display, for example and as shown in FIG. 3, a battery life. The local communicators 340 may also include a status light 344, a microphone 346 (for recording sounds from the medical emergency or for the operator 130 to ask questions of the medical professional 136 connected via the bi-directional communication 134), and/or a speaker (to sound an alarm to indicate an emergency, to sound a tone to indicate the defibrillator 104 is in need of service, to issue a set of directions to the medical emergency, and/or to relay the message of the medical professional 136 to the operator 130).

The power source 315 may be a battery, a direct current, and/or an alternating current. In one or more embodiments, the battery may be powered through an alkaline zinc-manganese dioxide compound (Zn/MnO2). The battery may also be a lithium-ion battery, and/or a rechargeable battery. The direct current may derive, for example, from a solar array associated with the communication module 102.

The communication module 102 may also have the set of sensors 308. For example, the temperature sensor 310 may sense the temperature of the communication module 102, the defibrillator 104, and/or the surrounding vicinity of either. A temperature reading may be useful to the organization 126 because a set of pads associated with the defibrillator 104 when exposed to a cold temperature may fail to stick to a chest area of the victim during the medical emergency. Additionally, the defibrillator 104 may fail when exposed to a hot temperature (e.g., 120 degrees) for prolonged periods. Similarly, the humidity sensor 312 may provide information relevant to the operational state and/or the operational status of the communication module 102 and/or the defibrillator 104. The luminescence sensor 314 may be a sensor detecting a lumens value of the light surrounding the communication module 102.

The storage 311 may include the settings data 122 sent to the communication module 102 by the central server 100. The settings data 122 may include the predetermined time interval 205. In one embodiment, the settings data 122 may cause the communication module 102 to enter an "awake" mode to communicate with the central server 100 when an ambient monitoring of the one or more of the set of sensors 308 that may reach a certain threshold value (e.g., the temperature drops below a freezing level).

Additionally, the communication module 102 have an associated unique identifier 112, which may, for example, be a number associated with a SIM card, a MAC address, a permanently assigned IP address, or any other uniquely identifying mark capable as being conveyed in digital form. It may exist in the storage 311 and may be contained in a hardware element of the communication module 102. The clock 316 and the timer 318 may be used by the communication module 102 to determine, in conjunction with the predetermined time interval 205, when the communication module 102 should attempt to withdraw from a sleep mode and attempt to connect with the central server 100. The clock 316 and/or the timer 318 may be always on, even when the communication module 102 is in a complete power down mode, but may consume a minimal amount of the power source 315.

The antenna 313 may be an antenna to communicate with the cellular network 103 and/or the wide area network 101 (for example, through communication with a wireless router of a local area network (LAN) of the organization 126). The communication module 102 may have a 2G, 3G or 4G LTE network capability. In one preferred embodiment, the communication module 102 may have a 2G capability to minimize data usage over the cellular network 103. In another preferred embodiment which may be required to enable the bi-directional communication 134, the communication module 102 may have at least the 3G capability.

The state library 322 may include a plurality of states and/or statuses (e.g., the operational state 114) of the functionality of the communication module 102 and/or the defibrillator 104. In the embodiment of FIG. 3, the state library 322 contains a set of states related to the operational state 114 of the communication module 102. The functional state 324 may be included in the message 110 to indicate that the communication module 102 may be in working order. For example, the communication module 102 may complete a diagnostic circuit check, a temperature reading by the temperature sensor 310, and a check to ensure that the camera 300 is in proper alignment with the display 302. Rather than communicate a result of these specific tests to the central server 100, the communication module may determine (e.g., on the "client side") that the communication module 102 is in a condition suitable to maintain deployment as part of the heterogeneous network 140. The functional state 324 may then be included in the contents of the message 110 and appropriately logged by the central server 100. In contrast, the service state 326 may be a state that that the communication module 102 conveys to the central server 100 when a functional error has occurred within the communication module 102. For example, the service state 326 may be signaled when the visual inspection 306 is hindered by an obstruction, when a sensor data from the set of sensors 308 cannot be interpreted, or when a self-diagnostic check is failed. Similarly, the tampered state 328 may be relayed to the central server as part of the operational state 114 of the message 110 when the communication module 102 determines that the communication module 102 and/or the defibrillator 104 has been utilized in a way inconsistent with normal operational use. For example, the tampered state 328 may be triggered when the housing 106 (not shown in the embodiment of FIG. 3) remains open for a period of over one week, when a magnet seal is broken on a compartment containing the internal components of the communication module 102, or when the voltage of the power source drops more rapidly than anticipated over a given period of time (which may indicate the battery is inferior when compared to a mandated specification).

The open status 330 may be the operational state 114 conveyed in the message 110 to alert the central server 100 that the housing 106 of the communication module 102 and/or the defibrillator 104 may be in the open state 132. In one embodiment, the communication module 102 may awaken from a sleep mode and immediately attempt to access the central server 100, at which time it may attempt to convey the open status 330. In one embodiment, sending of the open status 330 may preclude inclusion of other data items such as the visual inspection data 116 but may cause the inclusion of additional data items such as a live feed of sound collected by the microphone 346 and transmitted from the communication module 102 to the central server 100. The non-functional state 332 may be a data conveyed to the central server 100 when a failure occurs within the communication module 102. For example, the non-functional state 332 may result when a weak and/or an intermittent connection is formed with one of the networks, where an internal diagnostic is failed, and/or when a data contained in the storage 311 is corrupted. In one embodiment, two or more consistent states may be conveyed simultaneous (e.g., the service state 326 and the non-functional state 332). It should be noted that the operational status of the defibrillator 104, not shown in FIG. 3, may have analogous statuses to those of the operational state 114 of the communication module 102. For example, the operational status may be "a tampered status" and/or "a non-functional status."

The housing 106 of the defibrillator 104 (not shown in FIG. 3), if enclosing or encapsulating the defibrillator 104, may include features to allow the display 302 to be read at the location of the defibrillator 104 without removing the housing 106. For example, the housing 106 may include a number of clear windows in the housing 106 positioned such that the display 302 may be observed without opening the housing 106. The camera 300 and the display light 304 may be positioned at an angle such that the windows of the housing 106 allowing outside viewing of the display 302 are not obstructed.

In one embodiment not shown in FIG. 3, the communication module 102 may be integrated into the defibrillator 104. In such case, the camera 300 may be unnecessary (and the message 110 need not contain the visual inspection data 116) as the state library 322 may be sufficient to determine the operational state and/or operational status of the defibrillator 104.

Figure 4:
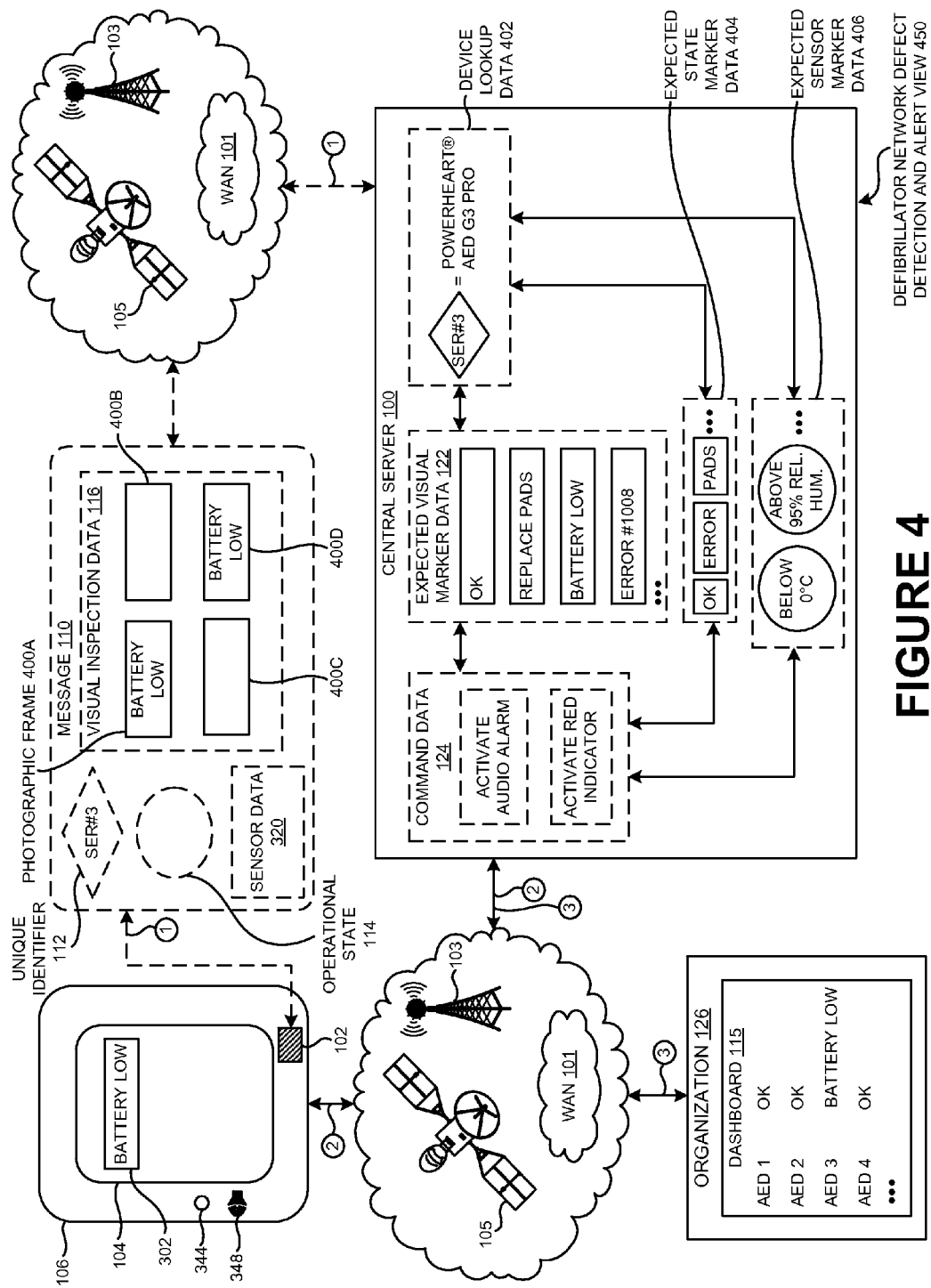
FIG. 4 is a defibrillator network defect detection and alert view 450 that shows the defibrillator of FIG. 1 communicating the message containing the visual inspection data comprised of a photographic frame, taken by the camera of FIG. 3, of the display of the defibrillator reading "low battery", the frame relayed to the central server through the network and compared to the expected visual marker data, the central server responding by transmitting the command data across the network to activate an alarm of the defibrillator, and additionally notifying the organization, according to one or more embodiments.

FIG. 4 is a defibrillator network defect detection and alert view 450 that shows the defibrillator of FIG. 1 communicating the message containing the visual inspection data comprised of a photographic frame, taken by the camera of FIG. 3, of the display of the defibrillator reading "low battery", the frame relayed to the central server through the network and compared to the expected visual marker data, the central server responding by transmitting the command data across the network to activate an alarm of the defibrillator, and additionally notifying the organization, according to one or more embodiments. Particularly, FIG. 4 further illustrates a set of photographic frames 400A through 400D, an expected marker lookup 402, an expected state marker data 404, In FIG. 4, the visual inspection data 116 generated by the communication module 102 may include the photographic frames 400A through 400D, which in combination may form a short video (e.g., the video 334). The photographic frames 400A through 400D may therefore capture a flashing "battery low" status indicated on the display 302 of the defibrillator 104 that may be missed by a single photograph.

The message 110 may move along path 'circle 1' through the WAN 101, the cellular network 103, and/or the satellite network 105 to the central server 100. The communication server 100 may then analyze the message 110 to determine the expected visual markers data 120 matching the make and model of the defibrillator 104 associated with the communication module 102 that send the message 110 (the expected visual markers data 120 relevant to the make and model of the defibrillator 104 may also be referred to as the manufacturer display data 207 of FIG. 2). For example, a set of the unique identifiers 112 may allocated to a particular make and model of the defibrillator 104 such that the central server 100 may use a lookup table to determine which make and model is associated with the unique identifier 112. The central server 100 may the compare the expected visual marker data 120 to the visual inspection data 116 using the pixel algorithm of the pixel analysis module 200 (not shown in the embodiment of FIG. 4). When a match is determined between at least one of the photographic frames 400 (e.g., the photographic frame 400A and 400D), the central server may issue the command data 124 which may have been set up to correspond to an expected visual markers within the expected visual marker data 120. For example, when the photographic frame 400A matched with the "battery low" expected visual marker, the command data 124 may be issued through one or more of the networks along path 'circle 2' to activate an audio alarm associated with the communication module and/or activate a red indicator light visible to an agent of the organization 126 in the presence of the defibrillator 104. The central server may also issue a notification (not shown in FIG. 4) to move through one or more of the networks along path 'circle 3' to the dashboard 115 of the organization 126. The dashboard 115 may be able to contain more detailed information about the operational state of the communication module 102 and/or the defibrillator 104 that may allow the agent of the organization, once having observed the activated red indicator light, check the dashboard 115 for information as to the particular malfunction or inoperable condition of the communication module 102 and/or defibrillator 104. In a process similar to that which was just described, other data contained within the message 110 such as the operational state 114 and the sensor data 320 may be compared to the expected state marker data 404 and the expected sensor marker data 406, respectively, to generate additional instances of the command data 124 and/or the update to the dashboard 115 of the organization 126.

The command data 124 may be issued by the operator of the central server 100 and/or the organization 126 to, for example, test the communication module 102 in response to an instance of the command data 124 or to warn users that a specific make and model of the defibrillators 104 has been recalled.

Figure 5:
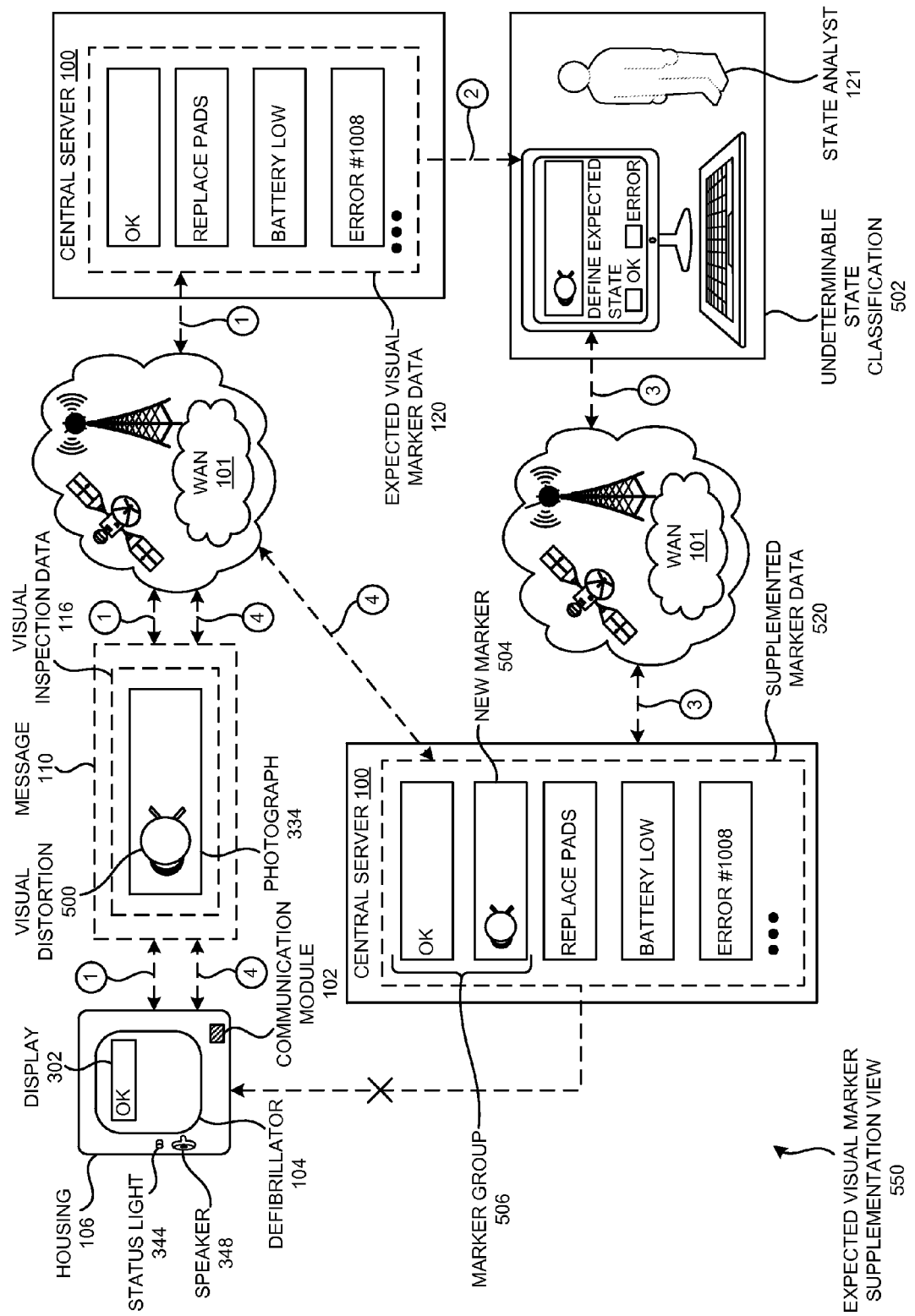
FIG. 5 is an expected visual marker supplementation view which shows the message of FIG. 1 containing a photograph of the display marred by a visual distortion, the photograph forwarded by the central server to a state analyst for an undeterminable state classification, the state analyst defining a new marker and adding the new marker to the expected visual marker data to form a supplemented marker data such that the visual distortion will be prospectively interpreted automatically and accurately by the central server, according to one or more embodiments.

FIG. 5 is an expected visual marker supplementation view which shows the message of FIG. 1 containing a photograph of the display marred by a visual distortion, the photograph forwarded by the central server to a state analyst for an undeterminable state classification, the state analyst defining a new marker and adding the new marker to the expected visual marker data to form a supplemented marker data such that the visual distortion will be prospectively interpreted automatically and accurately by the central server, according to one or more embodiments. Particularly, FIG. 5 further illustrates a visual distortion 500 within the photograph 333 of the display 302, an undeterminable state classification 502, a new marker 504, a marker group 506, and a supplemented marker data 520.

In FIG. 5, the photograph 333 includes a visual defect, the visual distortion 500. The visual distortion 500, for example, may occur due to improper alignment of the camera 300 with the display 302, as adverse lighting condition of the area surrounding the communication module (e.g., direct sunlight), and/or a defibrillator 104 having a smudged or scratched display 302. The visual distortion 500 illustrated in FIG. 5 may be a glare from the display light 304 being aligned at an improper angle due to the housing 106 being improperly closed. Specifically, the display 302 reads "ok" but the visual distortion obfuscates about one-half of each letter.

The message 110 containing the visual inspection data 116 containing the photograph 333 bearing the visual distortion 500 may be conveyed along path 'circle one' through one or more of the networks to the central server 100 and compared, in accordance with the procedure set forth in FIG. 4 using the pixel algorithm, with the expected visual marker data 120. The central server 100 may determine that no expected visual marker matching the photograph 333 bearing the visual distortion 500 exists in the database 111. When the central server 100 determines no match has occurred, it may forward part or all of the message 110 along path 'circle 2' to the state analyst 121. The state analyst 121 may observe the visual inspection data 116, compare the visual inspection data 116 to the rest of the context of the message 110, and compare the contents of the message 110 to the log data 202 (e.g., the audit trail data 203 and/or the message records data 204). In reviewing a history and a context in which the message 110 was generated, and in viewing the photograph 333 with the visual distortion 500, the state analyst 121 may complete the undeterminable state classification 502 that may create the new marker 504 and add it to the expected visual marker data 120 along page 'circle 3.' The new marker 504 may be added to the marker group 506 such that the same set of command data 124 and/or updates to the dashboard 115 may result from the matching of prospective instances of the visual inspection data 116 to any marker within the marker group 506. Here, the state analyst 121 classified the photograph 333 bearing the visual distortion 500 as being within the marker group 506 of an "ok" defibrillator status. The expected visual marker data 120, once the new marker 504 is added by the state analyst 121, may be known as the supplemented marker data 520.

Following creation of the supplemented marker data 520, a repeated instance of the message 110 may move along path 'circle 4' through one or more of the networks to the central server 100 (in FIG. 5, the same instance of the central server 100 is shown twice for the purpose of clarity). The central server 100 may compare the photograph 333 bearing a same or a similar instance of the visual distortion 500 and, determining that the expected visual marker (e.g., the new marker 504) exists, may decide not to issue the command data 124, not to forward the message 110 to the state analyst, and/or not to issue the notification to the dashboard 115 of the organization 126.

FIG. 6 is an organization dashboard user interface view 650 which shows a browser-based user interface of a dashboard presented to the organization of FIG. 1 such that an agent of the organization may review the heterogeneous network of defibrillators, including a unique identifier of the defibrillator, a status of the defibrillator, a current geospatial location, a settings, a communication module battery life, and a last serviced date, according to one or more embodiments. Specifically, FIG. 6 further illustrates a local AED ID 600, a make 602 and a model 604, an AED state 606 which may include a status 608 and a message 610, a location 612 which may include an association 614 and a current geospatial coordinates 616, a settings 618, a communication module battery life 620, and a last serviced date 622.

The dashboard 115 may be a browser-based dashboard and/or user interface that allows an agent of the organization 126 to easily view their heterogeneous network 140 of defibrillators 104. Alternatively, the dashboard 115 may be a client-side application communicating with the central server 100. In FIG. 6, each of the defibrillators 104 of the heterogeneous network 140 may include the local AED ID 600 which may be a number defined by the organization 216 for internal tracking purposes. Each communication module 102 may also include the unique identifier 112, and the make 602 and model 604 of the associated defibrillator 104. The AED state 606 may show the status 608 of the AED (e.g., "ok," "error," "check"). The status 608 may additionally show more in-depth data related to either the operational state of either the communication module 102 and/or the operational status of the defibrillator 104. For example, the communication module 102 may be in the tampered state 328 and therefore the status 608 of the defibrillator 104 may be "unknown." Even more detailed information may appear in the message 610, for example the specific error such as a circuit malfunction. The message 610 may also include automatic links to view further details (such as the audit trail data 203 associated with the defibrillator 104) or send a technician to service and/or retrieve the defibrillator 104.

The location 612 may include the association 614 set by the organization 126 (e.g., "Factory 1, first floor lobby", "police car 5112"), and also the current geospatial coordinates 616 as determined, for example, by the global positioning circuit 108. The association 614 and the current geospatial coordinates 616 may not match as a result of the defibrillator 104 being conveyed from its place of association. The settings 618 may display the information related to the settings data 122, including the predetermined time interval 205. The settings 618 may display any other number of settings related to the communication module 102 and/or the defibrillator 104 having the integrated communication module 102, for example the current voltage settings of the defibrillator 104, which of the set of sensors 308 may be active, and which emergency features (e.g., the bi-directional communication 134) are enabled. The communication module battery life 620 may show the amount of the power source 315 of the communication module 102 that was remaining the last time the communication module 102 connected with the central server 100. The last serviced date 622 may show a date at which the defibrillator 104 and/or the communication module 102 was last checked for functionality (e.g., at the site of the association 614) by a technician, certifying expert, or any additional personnel that may be required by law to inspect the communication module 102 and/or defibrillator 104. The dashboard 115 may contain a number of additional fields conveying useful information to the organization 126 and/or allowing interaction with the defibrillators 104 of the heterogeneous network 140.

FIG. 7 is a defibrillator emergency response view which shows a medical incident in which a victim may be suffering from a cardiac arrest, the medical incident precipitating an emergency call to a medical facility and automatically triggering nearby defibrillators, through the central server communicatively coupled to the network receiving the emergency call, to sound a response such as an alarm, a voice alert, and a set of emergency directions, according to one or more embodiments. Particularly, FIG. 7 further illustrates three defibrillators 104X through 104Z, a cardiac arrest 700, a router 701, an emergency call 702, a medical facility 704, an emergency vehicle 706, a police car 708, an alarm 710, a voice alert 712, and an emergency directions 714.

FIG. 7 shows the increased ability the capability the defibrillator monitoring and response network 150 may have to save lives. In the example of FIG. 7, the cardiac arrest 700 may occur on the 200 block of University Avenue in Palo Alto, Calif. The cardiac arrest 700 may be treatable with a defibrillator (e.g., the defibrillator 104) where one is readily available. A bystander may initiate the emergency call 702 from a mobile device, the emergency call 702 going through the cellular network 103 to the medical facility 704 which may dispatch the emergency vehicle 706.

The emergency vehicle 706 may not arrive in time. Uncorrected, the cardiac arrest may rapidly lead to irreversible brain damage and death in the victim 131. After approximately three to five minutes in cardiac arrest, the victim 131 may suffer irreversible brain and/or tissue damage. For every minute that the victim 131 may be in cardiac arrest, the chance of survival may decrease by 7 percent per minute in the first 3 minutes, and may decreases by as much as 10 percent per minute for times longer than three minutes. Bystanders may be unaware of the location of defibrillators, and those near defibrillators may be unaware of the cardiac arrest 700 or of the emergency call 702.

However, the emergency call 702 may automatically be communicated through the network to the central server 100, along with a cellular triangulation and/or GPS data regarding the location of the cardiac arrest 700. The emergency call 702 may be forwarded by the medical facility 704, or the operator of the central server 100 may have a pre-agreed local accessibility to distress calls such as the emergency call 702. In the alternative, the emergency call 702 may be replaced with an application of a mobile device (e.g., a cell phone, a tablet, a smartphone) that may directly communicate a geo-location of the cardiac arrest 700 to the central server 100 through one or more of the communication networks.

The emergency alert module 216 of the central server 100 may then send command data 124 to activate a number of emergency features of the defibrillators 104 of the heterogeneous network 140 having current geospatial coordinates 616 (and/or geospatial location 118) within a threshold distance from the cardiac arrest 700 and/or location of the emergency call 702. The central server 100 may issue the command data 124 through the cellular network 103, and/or through the WAN 101 (which may, as shown in FIG. 7, communicate with the defibrillator 104A through the router 701 which may be a wireless router). These defibrillators 104X, 104Y and 104Z may reach the victim 131 faster than the emergency vehicle 706. Defibrillator 104X which may be located in the police car 708 about one block away from the cardiac arrest 700 may issue the alarm 710. The alarm 710 may alert a police officer in the police car 708 to check his police scanner and/or begin searching for the victim 131. The defibrillator 104Y may give even more specific instructions to anyone nearby, such as the voice alert 712 which may indicate an estimated distance to the victim 131 such as "cardiac arrest within 500 feet." Finally, the defibrillator 104Z, which may be located at a government post office, may issue the emergency directions 714 that may give those nearby an estimated address of the victim 131 and/or direction to get to an approximate location of the victim 131. For example, the emergency directions 714 may state "emergency on 200 block of University Avenue." Updated instructions may be issued by the central server 100 as the central server 100 follows the geospatial location 118 of the defibrillator issuing the emergency directions 714. Due to the efficiency of the defibrillator monitoring and response network, the victim 131 way be treated with the defibrillator 104X, 104Y or 104Z and may be prevented from serious brain damage or death.

Figure 8:
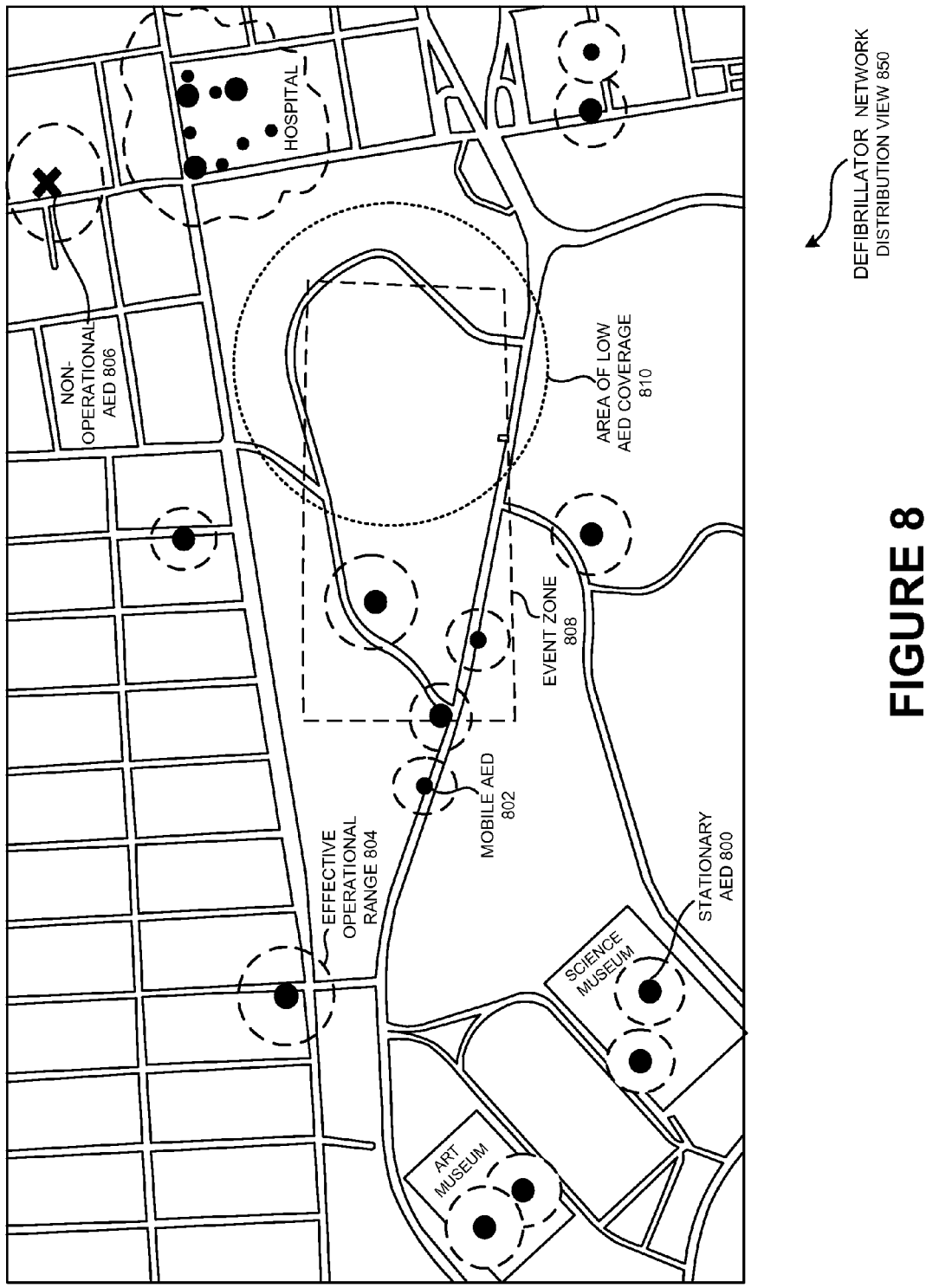
FIG. 8 is a defibrillator network distribution view which shows a graphical user interface (GUI) of a map of deployed defibrillators communicating with the defibrillator monitoring and response network of FIG. 1, the map including designations of a mobile AED, a stationary AED, a non-operational AED, and an effective operational range for each, the defibrillator network distribution view further illustrating identification of an area of low AED coverage within an event zone likely to contain a large number of people any of whom may be subject to the cardiac arrest of FIG. 7, according to one or more embodiments.

FIG. 8 is a defibrillator network distribution view which shows a graphical user interface (GUI) of a map of deployed defibrillators communicating with the defibrillator monitoring and response network of FIG. 1, the map including designations of a mobile AED, a stationary AED, a non-operational AED, and an effective operational range for each, the defibrillator network distribution view further illustrating identification of an area of low AED coverage within an event zone likely to contain a large number of people any of whom may be subject to the cardiac arrest of FIG. 7, according to one or more embodiments. Particularly, FIG. 8 further illustrates a stationary AED 800, a mobile AED 802 an effective operational range 804, a non-operational AED 806, an event zone 808, and an area of low AED coverage 810.

The central server 100 may include an API such that a map data of the heterogeneous network 140 of defibrillators 104 within the organization 126 may be available to the organization 126. In addition, multiple data sets, one for each organization 126 managed by the central server 100 may be exported to another larger instance of the organization 126, for example a local government (e.g., San Francisco). The map data may show visual representations of each defibrillator 104, for example that the stationary AED 800 is associated with a semi-permanent location (e.g., mounted to a wall, but still able to be removed and carried away from its mounted position), the mobile AED 802 (deployed in a vehicle), and the non-operational AED 806 (e.g., experiencing non-functional state 332). In addition, the map data may show the effective operational range 804 of each defibrillator 104, for example the average distance a person may be able to run with the defibrillator within a three-minute period of time. The defibrillators 104 displayed on the map data may allow one or more instances of the organization 126 to determine a area of low AED coverage 810, which may be especially relevant when the organization 126 expects a large number of people to be located in a single area, for example the event zone 808. The ability to view the distribution of defibrillators 104 of one or more of the organizations 126 may enable the efficient allocation of defibrillators to maximize the chance that any victim 131 will be within the effective operational range 804 of one of the defibrillators 104. The map data may be accessible, for example, through the dashboard 115, or may be shared and integrated with mapping services such as those offered by Google®.

FIG. 9 is a bi-directional defibrillator communication view which shows a defibrillator in use by an operator attempting to save a victim, a bi-directional communication of the defibrillator forming between the operator and one or more medical professionals associated with a medical facility and/or an emergency vehicle, a cellular network triangulation conveying an open AED location to the medical professional, the bi-directional communication additionally giving confidence to the operator such that operator uses the defibrillator in the absence of the medical professionals, according to one or more embodiments. Particularly, FIG. 9 further illustrates a cellular network triangulation 900, a communication device 902, an AED tracking map 904, and an open AED location 906.

In FIG. 9, the defibrillator 104 in the open state 132 may have connected with the central server 100 using the communication module 102. The central server 100 may establish the bi-directional communication 134 between the medical professional 136 of the medical facility 704 and/or the medical professional 136 of the emergency vehicle 706. The medical facility 704 may be a hospital, a doctor's office, an urgent care facility, a surgical center, and/or another other facility that may have the medical professional 136 on staff in his or her official capacity. The emergency vehicle may be an ambulance, a fire truck, a police vehicle, or another vehicle that may be dispatched such as a park ranger's truck or a rescue helicopter.

The operator 130 may be reluctant to use the defibrillator 104 on the victim 131 for fear that the victim 131 may suffer a greater injury. For example, in the comment of 'circle 1' the operator 130 expresses a doubt about knowing whether the victim 131's condition is the cardiac arrest 700 or whether the victim 131's condition is a heart attack (which may not be treatable by a defibrillation). In the comment of 'circle 2', the bi-directional communication 134 may convey the doubt to the medical professionals 136. The medical professional 136 of the medical facility 704 may then reassure the operator 130 in the comment of 'circle 3' and 'circle 4' that the defibrillator 104 may automatically detect whether the condition is treatable with the defibrillator 104. Further, in the comment of 'circle 5' and 'circle 6', the medical professional 136 may further instill confidence in the operator 130 through use of the communication device 902 (which may be a cell phone or other wireless device) by notifying the operator 130 that the emergency vehicle 706 will arrive shortly.

In addition, the geospatial location 118 of the communication module 102 of the defibrillator 104 may be conveyed through the satellite network (or the current geospatial coordinates 616 determined through the cellular network triangulation 900) and related to one or more of the medical professionals 136 such that the open AED location 906 may be observed in the AED tracking map 904. The AED tracking map 904 may be, for example, integrated into the emergency vehicle 706, or may be viewable on the communication device 902 of the medical professional 136.

What is claimed is:

1. A monitoring system comprising:
a defibrillator having a communication module to periodically generate a message based on an operational status of the defibrillator;
a network;
a central server communicatively coupled with the communication module of the defibrillator through the network to analyze the message and to perform an action based on the operational status of the defibrillator; and
wherein the central server to determine an operational status of the defibrillator based on a comparison of at least one of a photograph and a video to a set of expected visual markers using a pixel algorithm of a pixel analysis capability of the central server.

2. The monitoring system of claim 1:
wherein the communication module to automatically enter an active mode from a sleep mode based on a predetermined time interval and to compress the message prior to communicating the message using a cellular network topology of the network in a manner such that a battery life of at least one of the communication module and the defibrillator is maintained for at least five years, and
wherein the battery is powered through at least one of an alkaline zinc-manganese dioxide compound (Zn/MnO2), a rechargeable battery, a solar powered battery, and an alternating current source (A/C).

3. The monitoring system of claim 2:
wherein the defibrillator is enclosed in a housing in which the communication module is attached, and
wherein the housing to monitor the operational state of the defibrillator through a visual inspection of a display of the defibrillator that is enclosed in the housing.

4. The monitoring system of claim 3:
wherein the housing is designed to operate across a wide range of defibrillator manufacturers such that defibrillators of different defibrillator manufacturers are each enclosed in housings having a common version of the communication module,
wherein the central server to monitor the operational status of a heterogeneous network of defibrillators made by different manufacturers without requiring normalization of disparate communication modalities, and
wherein disparate communication modalities of different manufacturers is obviated as a result of the common version of the communication module.

5. The monitoring system of claim 4:
wherein the housing to include at least one of a camera, a temperature sensor, a humidity sensor, a luminescence sensor, a clock, a timer, a global positioning circuit, a microphone, a speaker, an status light, and a display light,
wherein at least one of the camera, the temperature sensor, the humidity sensor, the luminescence sensor, the clock, the timer, the global positioning circuit, the microphone, the speaker, the status light, and the display light to activate when the communication module periodically enters the active mode from the sleep mode, and
wherein the sleep mode is a complete power down of the communication module.

6. The monitoring system of claim 5:
wherein the display light to illuminate the display based on at least one of a time of day as detected through the clock, a lumens value being below a threshold value as calculated by the luminescence sensor during the active mode of the communication module, and a visual readability of the display, and
wherein the camera to take at least one of a photograph of the display and a video of the display and to communicate at least one of the photograph of the display and the video of the display to the central server.

7. The monitoring system of claim 6 further comprising:
wherein the central server to analyze at least one of the photograph of the display and the video to determine an operational status of the defibrillator using a pixel algorithm of a pixel analysis module based on a set of expected visual markers based on a model and a manufacturer of the defibrillator associated with the housing,
wherein the central server to determine that the communication module is in at least one of a functional state, a service state, a tampered state, an open state and a nonfunctional state,
wherein the central server to determine that the defibrillator is in at least one of a functional status, a service status, a tampered status, an open status and a nonfunctional status,
wherein the central server to forward at least one of the photograph of the display and the video of the display to a state analyst to verify the operational status of the defibrillator when the central server determines that the defibrillator is in at least one of the service state, the tampered state, the open state, and the nonfunctional state, and
wherein the central server to supplement the set of expected visual markers with at least one of the photograph verified by the state analyst and the video verified by the state analyst to enhance a veracity of an operational status determination analysis by the central server.

8. The monitoring system of claim 7 further comprising:
wherein the communication module to override the periodic awakening and to automatically enter the active mode from the sleep mode when the defibrillator is in the open state,
wherein the central server to establish a bi-directional communication through the cellular network between a medical professional and an operator of the defibrillator when the defibrillator is in the open state, and
wherein the predetermined time interval is one day.

9. The monitoring system of claim 8 further comprising:
wherein the central server to determine a present geospatial location of the defibrillator using at least one of the global positioning circuit and a cellular device triangulation of the communication module,
wherein the central server to automatically generate an audio command to sound an audio alarm through the speaker of the housing when a 911 emergency call is detected in a geospatial vicinity closest to a defibrillator having at least one of an internal version of the communication module and an external version of the communication module in the housing,
wherein the audio alarm to also sound in alternatively a different audio frequency and tone when the defibrillator is in need of service, wherein the central server to automatically generate a status command to illuminate the status light of the housing when the 911 emergency call is detected in the geospatial vicinity closest to the defibrillator having at least one of the internal version of the communication module and the communication module in the housing, and wherein the status light to also illuminate in alternatively a different color and alternatively in a blinking pattern when the defibrillator is in need of service.

10. The monitoring system of claim 9 further comprising:

wherein the central server to assess a subscription fee to an organization that at least one owns and leases the defibrillator, wherein the subscription fee is based on a set of features desired by the organization, a service frequency, and a total number of installed defibrillators monitored by the central server on behalf of the organization, wherein the central server to automatically dispatch a technician to either reset defibrillators and repair defibrillators which are in at least one of the service status, the tampered status, the open status and the nonfunctional status, wherein the central server to provide a dashboard view to the organization such that the organization is permitted to view operational statuses of defibrillators deployed at different geospatial locations of the organization simultaneously, wherein the central server to automatically maintain an audit trail of defibrillators to maintain regulatory compliance based on the dashboard view, wherein the central server to periodically process a series of messages from communication modules of deployed defibrillators associated with the organization, wherein each one of the communication modules each include a unique identifier, and wherein the central server to determine the operational status of each of the deployed defibrillators based on an analysis of the series of messages with a lookup table based on the model and the manufacturer of each one of the deployed defibrillators as determined through the unique identifier of each one of the communication modules.

11. A method of a central server comprising:

processing a message generated by a communication module of a defibrillator associated with an organization wherein the communication module includes a unique identifier;

determining a manufacturer and a model of the defibrillator through a lookup table associating the manufacturer and the model with the unique identifier of the communication module;

analyzing at least one of a photograph and a video taken by the communication module of the defibrillator based on a set of expected visual markers based on the manufacturer and the model of the defibrillator; and determining an operational status of the defibrillator based on a comparison of at least one of the photograph and the video to the set of expected visual markers using a pixel algorithm of a pixel analysis module, wherein the operational status of the defibrillator is at least one of least one of a functional status, a service status, a tampered status, an open status and a nonfunctional status.

12. The method of claim 11 further comprising:

providing a dashboard view to the organization such that the organization is permitted to view operational statues of a set of the defibrillators deployed at different geospatial locations of the organization simultaneously; and automatically maintaining an audit trail of deployed defibrillators to maintain regulatory compliance based on the dashboard view.

13. The method of claim 12 further comprising:

assessing a subscription fee to the organization based on a number of messages processed by the central server;

automatically entering an active mode from asleep mode based on an open state of the deployed defibrillator;

establishing a bi-directional communication through a cellular network between a medical professional and an operator of the defibrillator in the active mode;

determining a present geo-spatial location of the defibrillator using at least one of the global positioning circuit and a cellular device triangulation of each of the communication modules, automatically generating an audio command to sound an audio alarm through the speaker of a housing of the deployed defibrillator in the active mode when a 911 emergency call is detected in a threshold geospatial distance to the defibrillator;

wherein the audio alarm to also sound in alternatively a different audio frequency and tone when the defibrillator is in need of service, wherein the central server to automatically generate a status command to illuminate the status light of the housing when the 911 emergency call is detected in the threshold geospatial distance to the defibrillator having at least one of the internal version of the communication module and the external version of the communication module in the housing, and wherein the status light to also illuminate in alternatively a different color and alternatively in a blinking pattern when the defibrillator is in need of service.

14. The method of claim 13 further comprising:

automatically dispatching a technician to either reset defibrillators and repair defibrillators which are in at least one of the service status, the tampered status, the open status and the nonfunctional status.

15. The method of claim 14:

wherein the communication module to automatically enter an active mode from a sleep mode based on a time interval of once a day and to compress the message prior to communicating the message using a cellular network topology of the network in a manner such that a battery life of at least one of the communication module and the defibrillator is maintained for at least five years, and wherein the battery is powered through at least one of an alkaline zinc-manganese dioxide compound (Zn/MnO2), a rechargeable battery, a solar powered battery, and an alternating current source (A/C).

16. The method of claim 15:

wherein the defibrillator is enclosed in a housing in which the communication module is attached, wherein the housing to monitor the operational status of the defibrillator through a visual inspection of a display of the defibrillator that is enclosed in the housing, wherein the housing is designed to operate across a wide range of defibrillator manufacturers such that defibrillators of different defibrillator manufacturers are each enclosed in housings having a common version of the communication module, wherein the central server to monitor the operational status of a heterogeneous network of defibrillators made by different manufacturers without requiring normalization of disparate communication methodologies, wherein disparate communication methodologies of different manufacturers is obviated a result of the common version of the communication module, wherein the housing to include at least one of a camera, a temperature sensor, a humidity sensor, a luminescence sensor, a clock, a timer, a global positioning circuit, a microphone, a speaker, an status light, and a display light, wherein at least one of the camera, the temperature sensor, the humidity sensor, the luminescence sensor, the clock, the timer, the global positioning circuit, the microphone, the speaker, the status light, and the display light to activate when the communication module periodically enters the active mode from the sleep mode, wherein the sleep mode is a complete power down of the communication module, wherein the display light to illuminate the display based on at least one of a time of day as detected through the clock, a lumens value being below a threshold value as calculated by the luminescence sensor during the active mode of the communication module, and a visual readability of the display, and wherein the camera to take at least one of a photograph of the display and a video of the display, and to communicate at least one of the photograph and the video of the display to the central server.

17. A monitoring system comprising:

a defibrillator having a communication module to periodically generate a message based on an operational status of the defibrillator;

a network; and a central server communicatively coupled with the communication module of the defibrillator through the network to analyze the message and to perform an action based on the operational status of the defibrillator, wherein the central server to periodically process a series of messages from communication modules of deployed defibrillators associated with an organization, wherein each one of the communication modules each include a unique identifier, wherein the central server to determine the operational status of each of the deployed defibrillators based on an analysis of the series of messages with a lookup table based on the model and the manufacturer of each one of the deployed defibrillators as determined through the unique identifier of each one of the communication modules, and wherein the central server to determine the operational status of the defibrillator based on a comparison of at least one of a photograph and a video to a set of expected visual markers using a pixel algorithm of a pixel analysis capability of the central server.

18. The monitoring system of claim 17, further comprising:

a pixel analysis module to determine the operational status of the defibrillator based on a comparison of at least one of a photograph and a video to a set of expected visual markers using a pixel algorithm, and wherein the communication module to automatically enter an active mode from a sleep mode based on a time interval of once a day and to compress the message prior to communicating the message using a cellular network topology of the network in a manner such that a battery life of at least one of the communication module and the defibrillator is maintained for at least five years, and wherein the battery is powered through at least one of an alkaline zinc-manganese dioxide compound (Zn/MnO2), a rechargeable battery, a solar powered battery, and an alternating current source (A/C).

19. The monitoring system of claim 18:

wherein the defibrillator is enclosed in a housing in which the communication module is attached, and wherein the housing to monitor the operational status of the defibrillator through a visual inspection of a display of the defibrillator that is enclosed in the housing.

20. The monitoring system of claim 19:

wherein the housing is designed to operate across a wide range of defibrillator manufacturers such that defibrillators of different defibrillator manufacturers are each enclosed in housings having a common version of the communication module, wherein the central server to monitor the operational status of a heterogeneous network of defibrillators made by different manufacturers without requiring normalization of disparate communication modalities, and wherein disparate communication modalities of different manufacturers is obviated a result of the common version of the communication module.

21. A monitoring system comprising:

a defibrillator having a communication module to periodically generate a message based on an operational status of the defibrillator;

a network; and a central server communicatively coupled with the communication module of the defibrillator through the network to analyze the message and to perform an action based on the operational status of the defibrillator, wherein the defibrillator is enclosed in a housing in which the communication module is attached, wherein the housing to monitor the operational state of the defibrillator through a visual inspection of a display of the defibrillator that is enclosed in the housing, and wherein the central server to determine an operational status of the defibrillator based on a comparison of at least one of a photograph and a video to a set of expected visual markers using a pixel algorithm of a pixel analysis capability of the central server.

22. The monitoring system of claim 21:

wherein the communication module to automatically enter an active mode from a sleep mode based on a predetermined time interval and to compress the message prior to communicating the message using a cellular network topology of the network in a manner such that a battery life of at least one of the communication module and the defibrillator is maintained for at least five years, and wherein the battery is powered through at least one of an alkaline zinc-manganese dioxide compound (Zn/MnO2), a rechargeable battery, a solar powered battery, and an alternating current source (A/C).

23. The monitoring system of claim 22:

wherein the housing is designed to operate across a wide range of defibrillator manufacturers such that defibrillators of different defibrillator manufacturers are each enclosed in housings having a common version of the communication module, wherein the central server to monitor the operational status of a heterogeneous network of defibrillators made by different manufacturers without requiring normalization of disparate communication modalities, and wherein disparate communication modalities of different manufacturers is obviated as a result of the common version of the communication module.

24. The monitoring system of claim 23:
wherein the housing to include at least one of a camera, a temperature sensor, a humidity sensor, a luminescence sensor, a clock, a timer, a global positioning circuit, a microphone, a speaker, an status light, and a display light,
wherein at least one of the camera, the temperature sensor, the humidity sensor, the luminescence sensor, the clock, the timer, the global positioning circuit, the microphone, the speaker, the status light, and the display light to activate when the communication module periodically enters the active mode from the sleep mode, and
wherein the sleep mode is a complete power down of the communication module.

25. The monitoring system of claim 24:
wherein the display light to illuminate the display based on at least one of a time of day as detected through the clock, a lumens value being below a threshold value as calculated by the luminescence sensor during the active mode of the communication module, and a visual readability of the display, and
wherein the camera to take at least one of a photograph of the display and a video of the display and to communicate at least one of the photograph of the display and the video of the display to the central server.

26. The monitoring system of claim 25 further comprising:
wherein the central server to analyze at least one of the photograph of the display and the video to determine an operational status of the defibrillator using a pixel algorithm of a pixel analysis module based on a set of expected visual markers based on a model and a manufacturer of the defibrillator associated with the housing,
wherein the central server to determine that the communication module is in at least one of a functional state, a service state, a tampered state, an open state and a nonfunctional state,
wherein the central server to determine that the defibrillator is in at least one of a functional status, a service status, a tampered status, an open status and a nonfunctional status,
wherein the central server to forward at least one of the photograph of the display and the video of the display to a state analyst to verify the operational status of the defibrillator when the central server determines that the defibrillator is in at least one of the service state, the tampered state, the open state, and the nonfunctional state, and
wherein the central server to supplement the set of expected visual markers with at least one of the photograph verified by the state analyst and the video verified by the state analyst to enhance a veracity of an operational status determination analysis by the central server.

27. The monitoring system of claim 26 further comprising:
wherein the communication module to override the periodic awakening and to automatically enter the active mode from the sleep mode when the defibrillator is in the open state,
wherein the central server to establish a bi-directional communication through the cellular network between a medical professional and an operator of the defibrillator when the defibrillator is in the open state, and
wherein the predetermined time interval is one day.

28. The monitoring system of claim 27 further comprising:
wherein the central server to determine a present geospatial location of the defibrillator using at least one of the global positioning circuit and a cellular device triangulation of the communication module,
wherein the central server to automatically generate an audio command to sound an audio alarm through the speaker of the housing when a 911 emergency call is detected in a geospatial vicinity closest to a defibrillator having at least one of an internal version of the communication module and an external version of the communication module in the housing,
wherein the audio alarm to also sound in alternatively a different audio frequency and tone when the defibrillator is in need of service,
wherein the central server to automatically generate a status command to illuminate the status light of the housing when the 911 emergency call is detected in the geospatial vicinity closest to the defibrillator having at least one of the internal version of the communication module and the communication module in the housing, and
wherein the status light to also illuminate in alternatively a different color and alternatively in a blinking pattern when the defibrillator is in need of service.

29. The monitoring system of claim 28 further comprising:
wherein the central server to assess a subscription fee to an organization that at least one owns and leases the defibrillator,
wherein the subscription fee is based on a set of features desired by the organization, a service frequency, and a total number of installed defibrillators monitored by the central server on behalf of the organization,
wherein the central server to automatically dispatch a technician to either reset defibrillators and repair defibrillators which are in at least one of the service status, the tampered status, the open status and the nonfunctional status,
wherein the central server to provide a dashboard view to the organization such that the organization is permitted to view operational statuses of defibrillators deployed at different geospatial locations of the organization simultaneously,
wherein the central server to automatically maintain an audit trail of defibrillators to maintain regulatory compliance based on the dashboard view,
wherein the central server to periodically process a series of messages from communication modules of deployed defibrillators associated with the organization, wherein each one of the communication modules each include a unique identifier, and
wherein the central server to determine the operational status of each of the deployed defibrillators based on an analysis of the series of messages with a lookup table based on the model and the manufacturer of each one of the deployed defibrillators as determined through the unique identifier of each one of the communication modules.

30. A method of a central server comprising:
processing a message generated by a communication module of a defibrillator associated with an organization wherein the communication module includes a unique identifier;
determining a manufacturer and a model of the defibrillator through a lookup table associating the manufacturer and the model with the unique identifier of the communication module;
analyzing at least one of a photograph and a video taken by the communication module of the defibrillator based on a set of expected visual markers based on the manufacturer and the model of the defibrillator; and
determining an operational status of the defibrillator based on a comparison of at least one of the photograph and the video to the set of expected visual markers using a pixel algorithm of a pixel analysis module,
  wherein the operational status of the defibrillator is at least one of least one of a functional status, a service status, a tampered status, an open status and a non-functional status,
  wherein the defibrillator is enclosed in a housing in which the communication module is attached, and
  wherein the housing to monitor the operational state of the defibrillator through a visual inspection of a display of the defibrillator that is enclosed in the housing.

31. The method of claim 30 further comprising:
providing a dashboard view to the organization such that the organization is permitted to view operational statues of a set of the defibrillators deployed at different geospatial locations of the organization simultaneously; and
automatically maintaining an audit trail of deployed defibrillators to maintain regulatory compliance based on the dashboard view.

32. The method of claim 31 further comprising:
assessing a subscription fee to the organization based on a number of messages processed by the central server;
automatically entering an active mode from asleep mode based on an open state of the deployed defibrillator;
establishing a bi-directional communication through a cellular network between a medical professional and an operator of the defibrillator in the active mode;
determining a present geo-spatial location of the defibrillator using at least one of the global positioning circuit and a cellular device triangulation of each of the communication modules,
automatically generating an audio command to sound an audio alarm through the speaker of the housing of the deployed defibrillator in the active mode when a 911 emergency call is detected in a threshold geospatial distance to the defibrillator;
wherein the audio alarm to also sound in alternatively a different audio frequency and tone when the defibrillator is in need of service,
wherein the central server to automatically generate a status command to illuminate the status light of the housing when the 911 emergency call is detected in the threshold geospatial distance to the defibrillator having at least one of the internal version of the communication module and the external version of the communication module in the housing, and
wherein the status light to also illuminate in alternatively a different color and alternatively in a blinking pattern when the defibrillator is in need of service.

33. The method of claim 32 further comprising:
automatically dispatching a technician to either reset defibrillators and repair defibrillators which are in at least one of the service status, the tampered status, the open status and the nonfunctional status.

34. The method of claim 33:
wherein the communication module to automatically enter an active mode from a sleep mode based on a time interval of once a day and to compress the message prior to communicating the message using a cellular network topology of the network in a manner such that a battery life of at least one of the communication module and the defibrillator is maintained for at least five years, and
wherein the battery is powered through at least one of an alkaline zinc-manganese dioxide compound (Zn/MnO2), a rechargeable battery, a solar powered battery, and an alternating current source (A/C).

35. The method of claim 34:
wherein the housing is designed to operate across a wide range of defibrillator manufacturers such that defibrillators of different defibrillator manufacturers are each enclosed in housings having a common version of the communication module,
wherein the central server to monitor the operational status of a heterogeneous network of defibrillators made by different manufacturers without requiring normalization of disparate communication methodologies,
wherein disparate communication methodologies of different manufacturers is obviated a result of the common version of the communication module,
wherein the housing to include at least one of a camera, a temperature sensor, a humidity sensor, a luminescence sensor, a clock, a timer, a global positioning circuit, a microphone, a speaker, an status light, and a display light,
wherein at least one of the camera, the temperature sensor, the humidity sensor, the luminescence sensor, the clock, the timer, the global positioning circuit, the microphone, the speaker, the status light, and the display light to activate when the communication module periodically enters the active mode from the sleep mode,
wherein the sleep mode is a complete power down of the communication module,
wherein the display light to illuminate the display based on at least one of a time of day as detected through the clock, a lumens value being below a threshold value as calculated by the luminescence sensor during the active mode of the communication module, and a visual readability of the display, and
wherein the camera to take at least one of a photograph of the display and a video of the display, and to communicate at least one of the photograph and the video of the display to the central server.

36. A monitoring system comprising:
a defibrillator having a communication module to periodically generate a message based on an operational status of the defibrillator;
a network;
a central server communicatively coupled with the communication module of the defibrillator through the network to analyze the message and to perform an action based on the operational status of the defibrillator; and
a pixel analysis module to determine the operational status of the defibrillator based on a comparison of at least one of a photograph and a video to a set of expected visual markers using a pixel algorithm,
wherein the central server to periodically process a series of messages from communication modules of deployed defibrillators associated with an organization,
wherein each one of the communication modules each include a unique identifier, and
wherein the central server to determine the operational status of each of the deployed defibrillators based on an analysis of the series of messages with a lookup table based on the model and the manufacturer of each one of the deployed defibrillators as determined through the unique identifier of each one of the communication modules,
wherein the defibrillator is enclosed in a housing in which the communication module is attached, and
wherein the housing to monitor the operational state of the defibrillator through a visual inspection of a display of the defibrillator that is enclosed in the housing.

37. The monitoring system of claim 36, further comprising:
- wherein the communication module to automatically enter an active mode from a sleep mode based on a time interval of once a day and to compress the message prior to communicating the message using a cellular network topology of the network in a manner such that a battery life of at least one of the communication module and the defibrillator is maintained for at least five years, and
- wherein the battery is powered through at least one of an alkaline zinc-manganese dioxide compound (Zn/MnO2), a rechargeable battery, a solar powered battery, and an alternating current source (A/C).

38. The monitoring system of claim 37:
- wherein the housing is designed to operate across a wide range of defibrillator manufacturers such that defibrillators of different defibrillator manufacturers are each enclosed in housings having a common version of the communication module,
- wherein the central server to monitor the operational status of a heterogeneous network of defibrillators made by different manufacturers without requiring normalization of disparate communication modalities, and
- wherein disparate communication modalities of different manufacturers is obviated a result of the common version of the communication module.

* * * * *